(12) United States Patent
Kennedy et al.

(10) Patent No.: US 11,293,746 B2
(45) Date of Patent: Apr. 5, 2022

(54) METHOD AND DEVICE FOR EVALUATING A MECHANICAL PROPERTY OF A MATERIAL

(71) Applicant: ONCORES MEDICAL PTY LTD, Crawley (AU)

(72) Inventors: Brendan Kennedy, Crawley (AU); Philip Wijesinghe, Crawley (AU)

(73) Assignee: ONCORES MEDICAL PTY LTD, Crawley (AU)

( * ) Notice: Subject to any disclaimer, the term of this patent is extended or adjusted under 35 U.S.C. 154(b) by 0 days.

(21) Appl. No.: 17/059,637

(22) PCT Filed: May 31, 2019

(86) PCT No.: PCT/AU2019/050558
§ 371 (c)(1),
(2) Date: Nov. 30, 2020

(87) PCT Pub. No.: WO2019/227170
PCT Pub. Date: Dec. 5, 2019

(65) Prior Publication Data
US 2021/0123715 A1    Apr. 29, 2021

(30) Foreign Application Priority Data
Jun. 1, 2018  (AU) ................................ 2018901981

(51) Int. Cl.
*G01B 9/02* (2022.01)
*A61B 5/00* (2006.01)
*G01B 11/16* (2006.01)

(52) U.S. Cl.
CPC .......... *G01B 9/0205* (2013.01); *A61B 5/0053* (2013.01); *G01B 9/02054* (2013.01);
(Continued)

(58) Field of Classification Search
CPC .............. G01B 9/02054; G01B 9/0205; G01B 11/161; A61B 2562/0266; A61B 5/0053
See application file for complete search history.

(56) References Cited

U.S. PATENT DOCUMENTS 9,968,294 B2 * 5/2018 Bichel .................. A61B 5/4836
10,228,297 B2 * 3/2019 McLaughlin ........ A61B 5/0053
(Continued)

FOREIGN PATENT DOCUMENTS

| EP | 0768516 A1 | 4/1997 |
|----|------------|--------|
| WO | 2001001849 A1 | 1/2001 |
| WO | 2016119011 A1 | 8/2016 |

OTHER PUBLICATIONS

International Search Report and Written Opinion mailed in International Patent Application No. PCT/AU2019/050558 dated Aug. 9, 2019 (7 pages).

*Primary Examiner* — Violeta A Prieto
(74) *Attorney, Agent, or Firm* — Michael Best & Friedrich LLP

(57) ABSTRACT

The present disclosure provides a method of evaluating a mechanical property of a material using a device for evaluating the mechanical property of the material. The device comprises a sensing layer having a thickness, a sensing surface and an opposite surface. The sensing layer is deformable such that, when the sensing surface is in direct or indirect contact with the material and a suitable load is applied across both the sensing layer and at least a portion of the material, the sensing layer deforms and the sensing surface moves relative to the opposite surface. The device also comprises a source of electromagnetic radiation in optical communication with the sensing layer. The source is arranged for generating electromagnetic radiation having a coherence length that is of the same order of magnitude as (Continued)

the thickness of the sensing layer or longer than the thickness of the sensing layer. Further, the device comprises a detector for detecting the electromagnetic radiation and being in optical communication with the sensing layer and arranged for receiving the electromagnetic radiation after the electromagnetic radiation is reflected at the interface at the sensing surface of the sensing layer. The method comprises positioning the sensing layer relative to the material such that the sensing surface is in direct or indirect contact with the material. Further, the method comprises applying the suitable load across both the sensing layer and at least a portion of the material whereby the sensing layer deforms and the interface at the sensing surface moves relative to a condition in which no load is applied. The method also comprises directing the electromagnetic radiation to the interface at the sensing surface such that at least a portion of the electromagnetic radiation is reflected at the interface at whereby a first signal is generated and directing electromagnetic radiation along a second optical pathlength to generate a second signal. Further, the method comprises allowing the first signal and the second signal to interfere and detecting an intensity associated with a resultant interference signal using the detector; and determining information concerning the mechanical property of the material from the detected intensity of the interference signal.

20 Claims, 15 Drawing Sheets

(52) U.S. Cl.
CPC .......... *G01B 11/161* (2013.01); *A61B 5/0066* (2013.01); *A61B 2562/0266* (2013.01)

(56) References Cited

U.S. PATENT DOCUMENTS

| | | | |
|---|---|---|---|
| 10,480,927 B2* | 11/2019 | Kennedy | G01B 11/161 |
| 2015/0297132 A1* | 10/2015 | Bichel | A61B 5/4836 |
| | | | 600/301 |
| 2016/0015271 A1 | 1/2016 | Wang et al. | |
| 2017/0328794 A1* | 11/2017 | McLaughlin | G01L 1/241 |
| 2018/0042480 A1 | 2/2018 | Liu | |
| 2019/0120608 A1* | 4/2019 | Kennedy | A61B 5/0066 |
| 2020/0273216 A1* | 8/2020 | Kennedy | A61B 1/00009 |
| 2021/0381823 A1* | 12/2021 | Kennedy | G01B 11/168 |

\* cited by examiner

METHOD AND DEVICE FOR EVALUATING A MECHANICAL PROPERTY OF A MATERIAL

FIELD OF THE INVENTION

The present invention broadly relates to an optical method and device for evaluating a mechanical property of a material.

BACKGROUND OF THE INVENTION

The present applicant has developed an optical palpation technique, which is disclosed in PCT international patent application no. PCT/AU2016/000019. The disclosed optical palpation (OP) technique developed can be used to distinguish between different material types, such as stiffer material or softer healthy. For example, the material may be biological tissue. In OP, a sensing layer is compressed against tissue material. The sensing layer deforms (changes thickness) based on the forces between the sensing layer and the tissue. Optical coherence tomography (OCT) is used to measure the layer thickness, particularly, the thickness before and after compression. Strain is estimated across the field of view. Stress or force is determined from the strain and a pre-characterised stress-strain response of the material.

The present invention provides further improvement.

SUMMARY OF THE INVENTION

In a first aspect of the present invention there is provided a method of evaluating a mechanical property of a material, the method comprising:
  providing the material;
  providing a device for evaluating the mechanical property of the material, the device comprising:
    a sensing layer having a thickness, a sensing surface and an opposite surface, the sensing layer being deformable such that, when the sensing surface is in direct or indirect contact with the material and a suitable load is applied across both the sensing layer and at least a portion of the material, the sensing layer deforms and the sensing surface moves relative to the opposite surface;
    a source of electromagnetic radiation in optical communication with the sensing layer, the source being arranged for generating electromagnetic radiation having a coherence length that is of the same order of magnitude as the thickness of the sensing layer or longer than the thickness of the sensing layer; and
    a detector for detecting the electromagnetic radiation and being in optical communication with the sensing layer and arranged for receiving the electromagnetic radiation after the electromagnetic radiation is reflected at the interface at the sensing surface of the sensing layer;
  the method further comprising:
  positioning the sensing layer relative to the material such that the sensing surface is in direct or indirect contact with the material;
  applying the suitable load across both the sensing layer and at least a portion of the material whereby the sensing layer deforms and the interface at the sensing surface moves relative to a condition in which no load is applied;
  directing the electromagnetic radiation to the interface at the sensing surface such that at least a portion of the electromagnetic radiation is reflected at the interface at whereby a first signal is generated;
  directing electromagnetic radiation along a second optical pathlength to generate a second signal;
  allowing the first signal and the second signal to interfere and detecting an intensity associated with a resultant interference signal using the detector; and
  determining information concerning the mechanical property of the material from the detected intensity of the interference signal.

The step of determining information concerning the mechanical property may comprise determining a relative position of the interface at the sensing surface, with the length of the second optical path being fixed prior to application of the load and with no variation in the length of the second optical path being required to measure a distance that an external layer boundary or internal boundary has moved due to the application of the suitable load.

The step of directing the electromagnetic radiation to the interface at the sensing surface may comprise directing the electromagnetic radiation into and through the sensing layer to the sensing surface.

The method in accordance with a specific embodiment of the present invention may further comprise determining a change in thickness of the sensing layer, the sensing layer having a predetermined known relaxed thickness being the thickness that the layer has when no load is applied, the change in thickness of the sensing layer being determined using the known relaxed thickness and a change in relative position of the interface at the sensing surface as a consequence of the deformation when the load is applied.

The step of determining information concerning the mechanical property of the material may comprise determining the change in thickness of the sensing layer from the detected intensity of the interference signal and determining the mechanical property of the material from the determined change in thickness of the sensing layer.

The method typically comprises determining the change in thickness of the sensing layer from a single interference signal. Alternatively, the method may comprise determining the change in thickness of the sensing layer from two interference signals, which may be generated by from reflections at top and bottom interfaces of the sensing layer.

The inventors have realised that knowledge concerning the deformation (change in thickness) of the sensing layer is sufficient to perform an optical palpation measurement. Consequently, it is not required to scan the entire depth of the sensing layer (as performed with OCT, which usually uses a broadband light source having a coherence length much shorter than the layer thickness) and a device for evaluating the mechanical property of the material may be simpler than an OCT device. For example, depending on the thickness of the sensing layer when it is uncompressed, there is no need for a broadband light source and a simpler narrower band light source (such as an LED) having a longer coherence length can be used. In addition, the optical detection can occur locally on a handheld implementation of the device for use in surgery, the detection time can be reduced and the device may be much smaller compared to an OCT system.

Determining information concerning the mechanical property of the material may comprise determining a change in an optical pathlength difference between the first signal and the second signal from a measured intensity of the detected interference signal in response to the suitable load applied to the sensing layer and the material. Further, determining the information concerning the mechanical property may comprise determining the information from the determined change in optical pathlength difference.

The inventors have recognized that the intensity of the detected interference signal from a specular reflector in the first optical path length as a function of the change in optical pathlength difference between the first signal and second may be considered as a Gaussian function for most light sources. There is consequently a relationship between change in sensing layer thickness and detected intensity. The thickness of the sensing layer (or a change in the thickness) can consequently be determined without the need for a depth-scanning (or depth sectioning) apparatus (such as an OCT apparatus).

The mechanical property may be elasticity or viscoelasticity and determining information concerning the mechanical property of the material may comprise determining stress experienced by the sensing layer based on the determined change in optical pathlength difference.

The source may be arranged for generating electromagnetic radiation having a coherence length that provides an interference signal for a range of different thicknesses of the sensing layer without adjusting the length of the second optical path.

The source of electromagnetic radiation may have a coherence length ranging from approximately the layer thickness to a few multiples of the layer thickness. For example, the source of electromagnetic radiation may have a coherence length greater than 30, 50, 70, 100 or 200 µm.

The opposite surface of the sensing layer may be a stationary surface that is stationary relative to a housing portion of the device when the suitable load is applied across both the sensing layer and at least a portion of the material. Alternatively, the opposite surface of the sensing layer may be moved or vibrated in a known manner.

Directing the electromagnetic radiation along the second optical path to generate the second signal may comprise directing the electromagnetic radiation to an interface at the opposite surface of the sensing layer and generating the second signal may comprise reflecting the electromagnetic radiation at the interface at the opposite surface.

Alternatively, directing the electromagnetic radiation along the second optical pathlength to generate the second signal may comprise directing the electromagnetic radiation to a mirror and generating the second signal may comprise reflecting the electromagnetic radiation at the mirror.

Detecting an intensity associated with the interference signal may also comprise detecting a time average of intensity and the method may comprise analysing the detected average intensity such that a change in thickness of the sensing layer can be determined at least largely independent from an angle of tilt between an optical pathlength and a relative orientation of the sensing layer, and/or from a focus condition of an optical signal at the sensing layer.

The device for evaluating the mechanical property of the material may further comprise a scanning mirror for scanning the first signal across the sensing surface of the sensing layer and the method may be conducted such that an image or a map of the sensing surface can be obtained, the image or map including features that are indicative of a distribution of the deformation across the sensing layer.

The device may alternatively comprise a vibrating or rotating optical fibre for scanning the first signal across the sensing surface of the sensing layer and the method may be conducted such that an image or a map of the sensing surface can be obtained, the image or map including features that are indicative of a distribution of the deformation across the sensing layer.

In another embodiment, the device comprises a plurality of optical fibres arranged to direct the electromagnetic radiation into the sensing layer to the sensing surface such that at least a portion of the electromagnetic radiation is reflected at the sensing surface to generate the first signal. In this embodiment, the method is conducted such that an image or a map of the sensing surface can be obtained.

The device for evaluating the mechanical property of the material may be a handheld device. The handheld device may be a finger-mounted or glove-based device.

Further, the device may comprise a wireless transmitter and may be arranged to transmit data in a wireless manner, for example for reception by a computer to process the data.

The step of directing electromagnetic radiation may comprise generating an oscillating signal of the electromagnetic radiation. Generating the oscillating signal may comprise applying an oscillation or vibration to the mirror and/or the sensing layer.

The device may further comprise polarisation controllers and polarisation filters to control a polarisation state of the first signal and of the second signal.

Detecting an intensity of a resultant interference signal may comprise detecting respective intensities associated with at least two polarisations.

The detector may comprise a polarising beam splitter arranged to split an optical signal indicative of the detected electromagnetic radiation into at least two signals having the respective polarisations.

The detector may further comprise respective detector portions for independent detection of the at least two signals having the respective polarisations.

The method may comprise analysing the detected light intensities having the respective polarisations in a manner such that a change in thickness of the sensing layer can be determined at least largely independent from an angle of tilt between an optical pathlength and a relative orientation of the sensing layer and/or a focus condition of the signal at the sensing layer.

Alternatively, detecting an intensity of a resultant interference signal may comprise detecting a time average of respective intensities associated with respective interference signals having respective phase contents.

In a further embodiment, determining information concerning the mechanical property of the material comprises determining a strain of the material as a result of the applied suitable load.

In a second aspect of the present invention there is provided a handheld device for evaluating a mechanical property a material, the device comprising:
  a sensing layer having a thickness, an exposed sensing surface and an opposite surface, the sensing layer being deformable such that, when the sensing surface is in direct or indirect contact with the material and a suitable load is applied across both the sensing layer and at least a portion of the material, the sensing layer deforms and the sensing surface moves relative to the opposite surface;
  a source of electromagnetic radiation in optical communication with the sensing layer, the source being arranged for generating electromagnetic radiation having a coherence length that is of the same order of magnitude as the thickness of the sensing layer or longer than the thickness of the sensing; and a detector for detecting the electromagnetic radiation and being in optical communication with the sensing layer, the detector being arranged for detecting electromagnetic radiation reflected at the interface at the sensing surface of the sensing layer;

wherein the device comprises:

a first optical pathlength in use providing a first signal, the first signal being a signal that is reflected at the sensing surface of the sensing layer; and a second optical pathlength in use providing second signal; and wherein the detector is positioned to detect both the first signal and the second signal whereby the detector detects in use an intensity associated with an interference signal and information concerning the mechanical property can be determined from the intensity of the interference signal.

The handheld device may be a finger-mounted or glove-based device.

The device may comprise a wireless transmitter and may be arranged to transmit data in a wireless manner, for example for reception by a computer to process the data.

The sensing layer may have a thickness ranging from a few micrometres to a few centimetres, such as from 10 μm to 3 cm when it is uncompressed, and consequently the sensing surface and the opposite surface may be separated from each other by a distance ranging from a few micrometres to a few centimetres, such as from 10 μm to 3 cm when the sensing layer is uncompressed.

The sensing layer may comprise, or may be formed from, translucent or transparent deformable material such as a gel, an elastomer.

The sensing layer may be a surgical sheath comprising a plastic material.

The source of electromagnetic radiation may be arranged for generating electromagnetic radiation having a coherence length that provides an interference signal for a range of different thicknesses of the sensing layer without adjusting the length of the second optical path.

The source of electromagnetic source may have a coherence length ranging from the thickness of the sensing layer to a length that corresponds to a multiple of the thickness of the sensing layer. For example, the source of electromagnetic radiation may have a coherence length greater than 30, 50, 70, 100 or 200 μm The thickness of the uncompressed sensing layer and the coherence length of the source used are typically chosen such that a variation in the intensity of the interference signal can be detected upon applying a suitable load across the sensing layer. A sensing layer having a relatively small thickness such as 10 μm and a light source having a corresponding relatively short coherence length may be used (similar to the coherence length of the broadband light source used in OCT). However, if the sensing layer is thicker and may for example have a thickness of a few centimetres, a light source having corresponding longer coherence length may be used.

The opposite surface of the sensing layer may be a stationary surface that is stationary relative to a housing portion of the device when the suitable load is applied across both the sensing layer and at least a portion of the material. Alternatively, the opposite surface of the sensing layer may be moved or vibrated in a known manner.

The second optical pathlength may comprise an interface at the opposite surface of the sensing layer whereby the second optical pathlength is arranged to generate the second signal by reflecting the electromagnetic radiation at the interface at the opposite surface.

Alternatively, the second optical pathlength may comprise a mirror and may be arranged to generate the second signal by reflecting the electromagnetic radiation at the mirror, which may be stationary relative to a housing portion of the device.

Alternatively, the mirror may be moved or vibrated in a known manner.

The device may further comprise a scanning mirror for scanning the first signal across the sensing surface of the sensing layer such that an image or map of the sensing surface can be obtained.

In one embodiment, the device comprises an oscillation or vibration element positioned at the mirror and/or the sensing layer for generation an oscillating electromagnetic radiation signal.

The device may further comprise polarisation controllers and polarisation filters to control a polarisation state of the first signal and of the second signal.

The second signal may be linearly polarised. The first signal may be circularly polarised.

The detector may comprise a polarising beam splitter arranged to split an optical signal indicative of the detected first signal and second signal into at least two signals having respective polarisations.

The detector may comprise respective detector portions for independent detection of the at least two signals having the respective polarisations.

The invention will be more fully understood from the following description of specific embodiments of the invention. The description is provided with reference to the accompanying drawings.

BRIEF DESCRIPTION OF DRAWINGS

Notwithstanding any other forms which may fall within the scope of the disclosure as set forth in the Summary, specific embodiments will now be described, by way of example only, with reference to the accompanying drawings in which.

DETAILED DESCRIPTION OF SPECIFIC EMBODIMENTS

Embodiments of the present invention relate to a method and a handheld device for performing an optical palpation measurement of a material. The person skilled in the art will appreciate that the material may take any suitable form. For example, the material may be an inorganic or an organic material. The material may also be biological tissue, such as ex-vivo or in-vivo biological tissue.

Optical palpation is a technique that can be used to map surface stress of the material and assist in distinguishing between different tissue types, such as cancerous tissue and usually softer healthy tissue. In optical palpation, a compressive load is applied to a sensing layer, which is positioned against the material. The sensing layer is compressed and deforms under the application of the compressive load, whereby the thickness of the sensing layer changes in response to the local stiffness of the underlying material. OCT is then used to image the change in thickness across the deformed sensing layer, which represents a stress distribution or map. This requires depth scanning (or depth sectioning) the entire thickness of the sensing layer.

However, while OCT scans the entire thickness of the sensing layer, the optical palpation technique only requires knowledge of the initial thickness of the sensing layer (before the load is applied) and information about a change in relative position of the interface between the sensing layer and the material in response to the application of the load. As a consequence, scanning the entire thickness of the sensing layer is not required. Further, depending on the initial thickness of the sensing layer before the load is applied there may be no need for a broadband light source. A simpler narrower band light source (such as an LED) having a longer coherence length may be used and a device for evaluating the mechanical property of the material using an optical palpation technique only can be relatively inexpensive and simpler compared with an OCT system. In addition, the device can be smaller and the detection time can be reduced compared with the detection time when an OCT system is used.

In accordance with embodiments of the present invention, there is disclosed a method and a handheld device for evaluating a mechanical property of a material. The mechanical property relates to the elasticity or stiffness of the material. Specifically, the elasticity may relate to a Young's modulus of the material, and the Young's modulus is representative of the stiffness of the material. In the medical field (as an example), it is known that abnormalities such as diseased tissue may alter the elasticity of biological tissue. For example, cancerous tissue is typically "stiffer" than surrounding healthy soft tissue. However, it will be understood that other mechanical properties may be evaluated such as viscoelasticity, anisotropy and poroelasticity.

Figure 1:
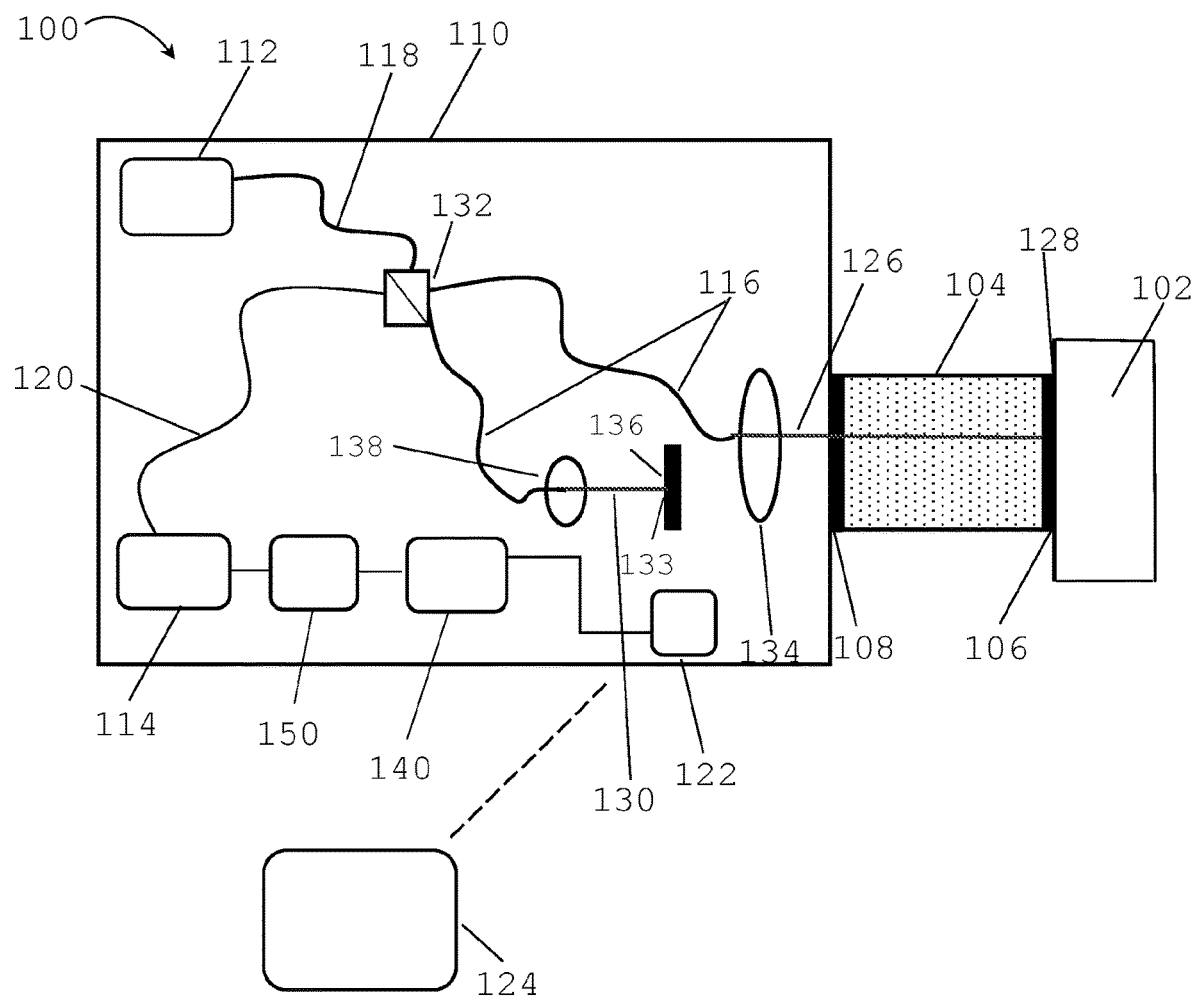
FIG. 1 is a schematic representation of a device for evaluating a mechanical property of a material in accordance with an embodiment of the present invention.

Referring now to FIG. 1, there is shown a handheld device 100 for evaluating elasticity of a material 102 in accordance with an embodiment of the present invention. It is noted that the handheld device 100 is in this specific embodiment in the form of a portable handheld device, however, it is envisaged that the handheld device be in the form of a finger-mounted or glove-based device.

The handheld device 100 comprises a sensing layer 104 having an exposed sensing surface 106 that is in this example positioned in direct contact with the material 102. The sensing layer 104 has a surface 108 that is opposite the sensing surface 106. The sensing layer 104 is deformable and comprises, in the present embodiment, a silicone material. However, it will be appreciated that the sensing layer 104 may alternatively also comprise any translucent or transparent deformable material such as a gel or an elastomer. It will also be appreciated that it is envisaged that when used during surgery, the sensing layer 104 may alternatively be a surgical sheath comprising a plastic material and used to cover the device 100. The device 100 further comprises a source 112 of electromagnetic radiation and a detector 114 for detecting electromagnetic radiation. Both the source 112 and the detector 114 are in optical communication with the sensing layer 104, by means of optical fibres 116, 118, and 120. In this embodiment, the device also comprises a wireless transmitter 122 for transmitting data in a wireless manner towards a computer 124 with which the data may be processed. The sensing layer 104 has in this specific embodiment a thickness of approximately 100 μm. However, it will be understood that the sensing layer 104 may have any other suitable thickness. For example, the sensing layer 104 may have a thickness in the range of 10 μm to 3 cm.

In another embodiment, the sensing surface 106 of the sensing layer 104 is in indirect contact with the material 102. For example, a thin layer comprising latex or another plastic material, such as a surgical sheath, may be positioned between the sensing surface 106 and the material 102 for preventing contamination of the material.

In this example, the source 112 emits electromagnetic radiation having a wavelength of around 1300 nanometres and having a bandwidth of 15 nanometres with a coherence length of approximately 50 micrometres. However, it is envisaged that the coherence length of the source 112 be in the range from 5 micrometres to a few millimetres and up to several centimetres.

The device 100 has an optical sample pathlength 126, which provides a sample signal. The sample signal is reflected at an interface 128 between the sensing surface 106 and the material 102. The device 100 also has an optical reference pathlength 130 in which electromagnetic radiation is directed to a reference mirror 133, which in this embodiment is stationary relative to the housing portion 110 of the device 100. The optical reference pathlength 130 provides a reference signal. The electromagnetic radiation that propagates along the sample pathlength 126 and reference pathlength 130 is focused by lenses 134 and 138, respectively.

The electromagnetic radiation emitted by the source 112 is distributed between the optical sample pathlength 126 and the optical reference pathlength 130 by optical beam splitter 132. The reflected electromagnetic radiation (both sample and reference) is allowed to interfere and detected by detector 114.

A suitable load is applied across the sensing layer 104 and a portion of the material 102, whereby the sensing layer 104 deforms and the sensing surface 106 moves relative to the opposite surface 108. The thickness of the compressed sensing layer 104 can be determined based on the interference intensities detected by the detector 114.

If the initial thickness of the (uncompressed) sensing layer 104 is known, then the change in thickness can be determined. Alternatively, the initial thickness of the sensing layer 104 may be determined in an analogous manner. Importantly, as the opposite surface 108 of the sensing layer 104 and the reference mirror 136 are in this embodiment stationary (relative to a housing portion of the device), the reference signal is constant and the device 100 allows obtaining information concerning the change in thickness of the sensing layer 104 in response to an applied load by analysing detected interference intensities. This is in contrast with an OCT system, for which depth sectioning of the entire thickness of the sensing layer is required to obtain information regarding the thickness of the sensing layer 104. The coherence length of the source 112 and the initial thickness of the sensing layer 104 are typically chosen in embodiments of the present invention such that a variation in the intensity of electromagnetic radiation received at the detector 114 can be detected upon application of the suitable load across the sensing layer 104.

In the present embodiment illustrated in FIG. 1, the device 100 further comprises an analog-to-digital converter 140 for digitising an output of the detector 114 and a wireless transmitter 122 for transmitting data from the device 100 to a computer 124.

Figure 2:
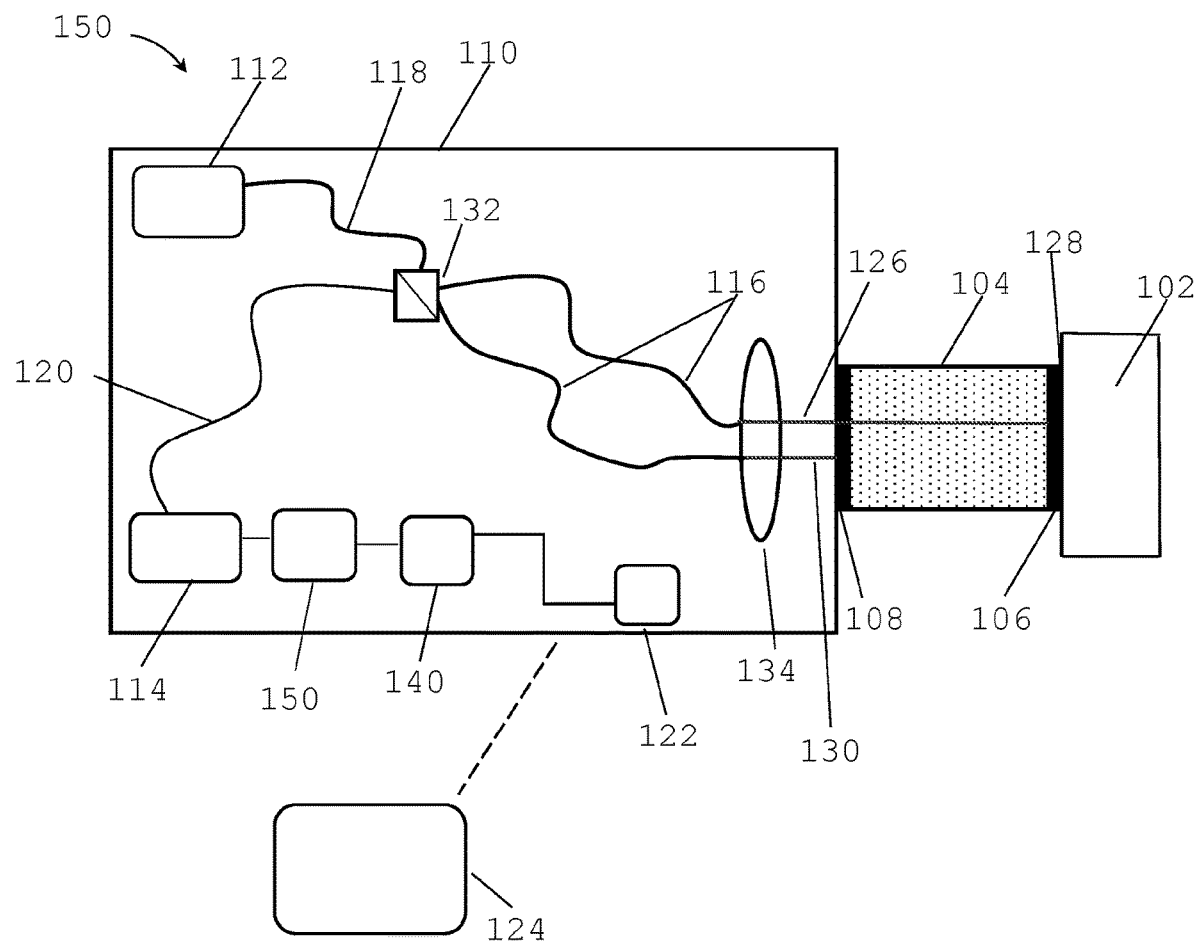
FIG. 2 is a schematic representation of a device for evaluating a mechanical property of a material in accordance with another embodiment of the present invention.

FIG. 2 shows a device 150 in accordance with an alternative embodiment of the present invention and like components are represented by like reference numerals. The optical reference pathlength provides in this embodiment a reference signal that is reflected at the opposite surface 108 of the sensing layer 104.

As mentioned above, the intensity of the detected interference signal as a function of change in optical pathlength difference between the sample signal and the reference signal may be considered as a Gaussian function. There is consequently a relationship between the detected interference intensity and the position of the interface 128, which can be used to measure the change in thickness of the sensing layer 104 as a result of the applied load without the need for a depth-sectioning apparatus, such as an OCT apparatus.

Figure 3A:
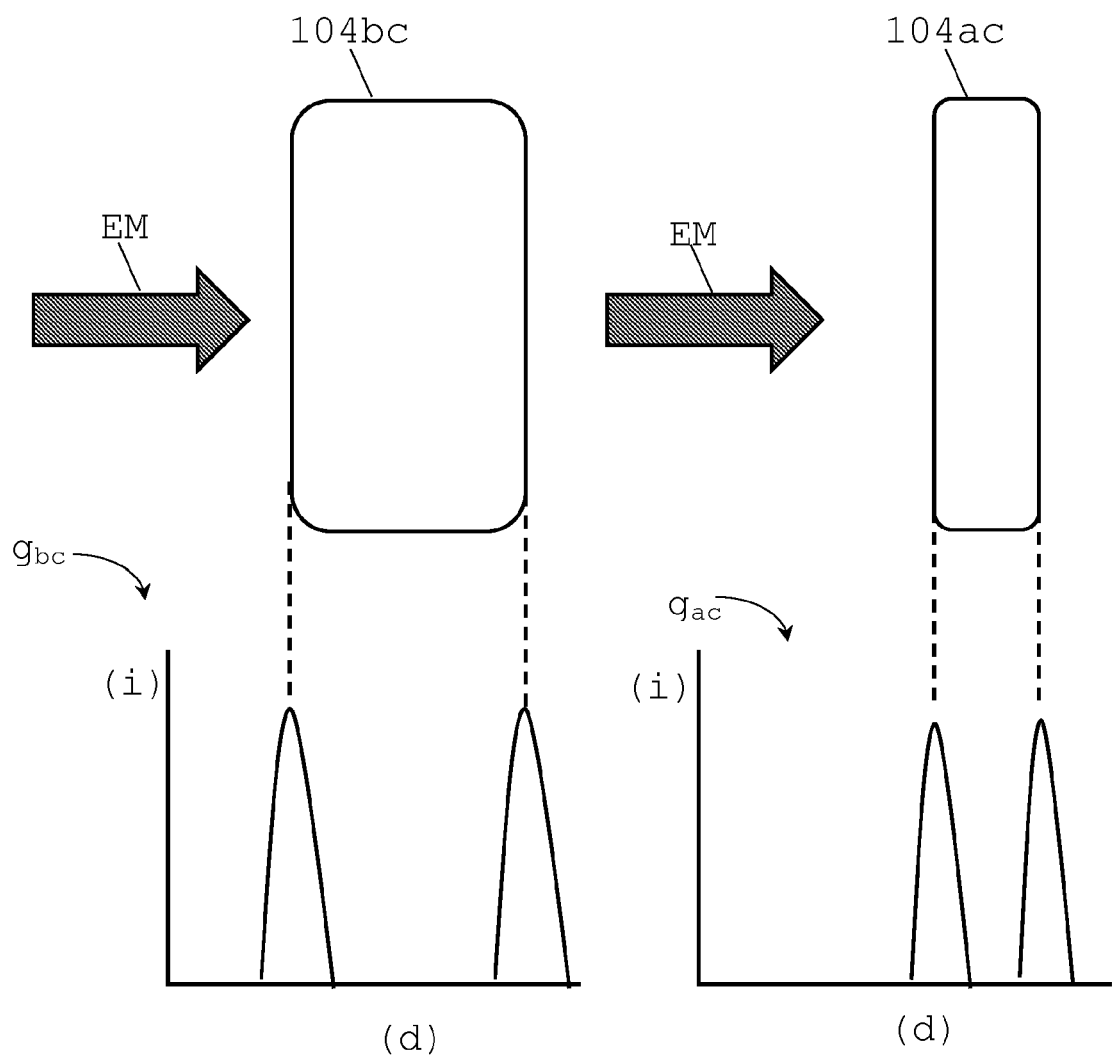
FIG. 3a is a diagram illustrating a known method of evaluating a mechanical property of a material using Optical Coherence Tomography.

Referring now to FIG. 3a, the known principle for determining a mechanical property of the material or a biological material using optical palpation using OCT is now illustrated before the method in accordance with embodiments of the present invention is illustrated. A broadband light source having a relatively short coherence length is used and emitted light is directed towards and through the sensing layer 104, as illustrated by arrow "EM". The thickness of the sensing layer 104 is measured before compression as illustrated by sensing layer 104bc. The graph $g_{bc}$ shows intensity measurements (i) of a detected interference signal as a function of depth (d). This comprises depth sectioning the entire thickness of the sensing layer 104bc (graph $g_{bc}$ only illustrates the interference intensities corresponding to the layer interfaces). The thickness of the sensing layer 104 is then measured after compression as illustrated by sensing layer 104ac and the graph $g_{ac}$ shows the corresponding interference intensities. Again, this comprises depth sectioning the entire thickness of the layer 104ac.

Figure 3B:
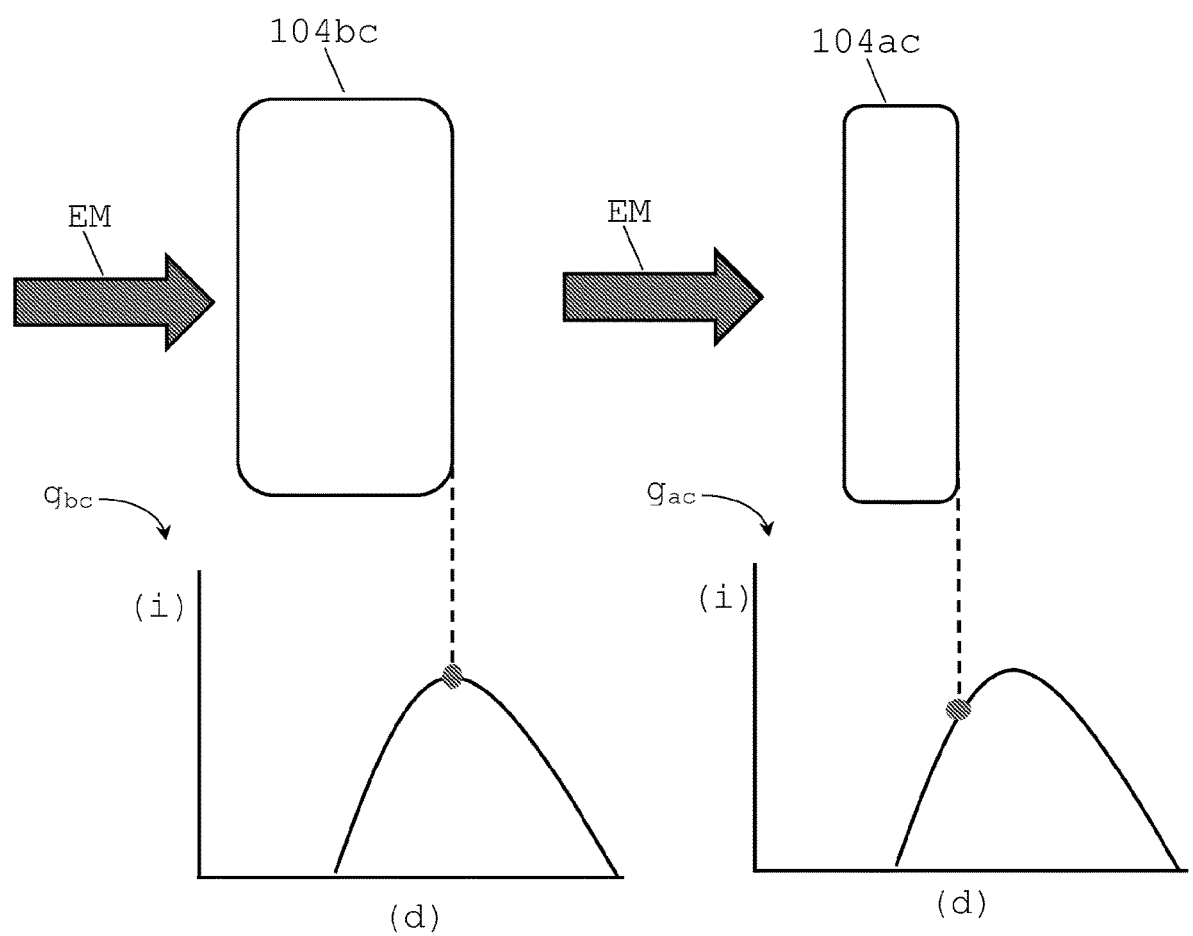
FIG. 3b is a diagram illustrating a method of evaluating a mechanical property in accordance with embodiments of the present invention.
Figure 4:
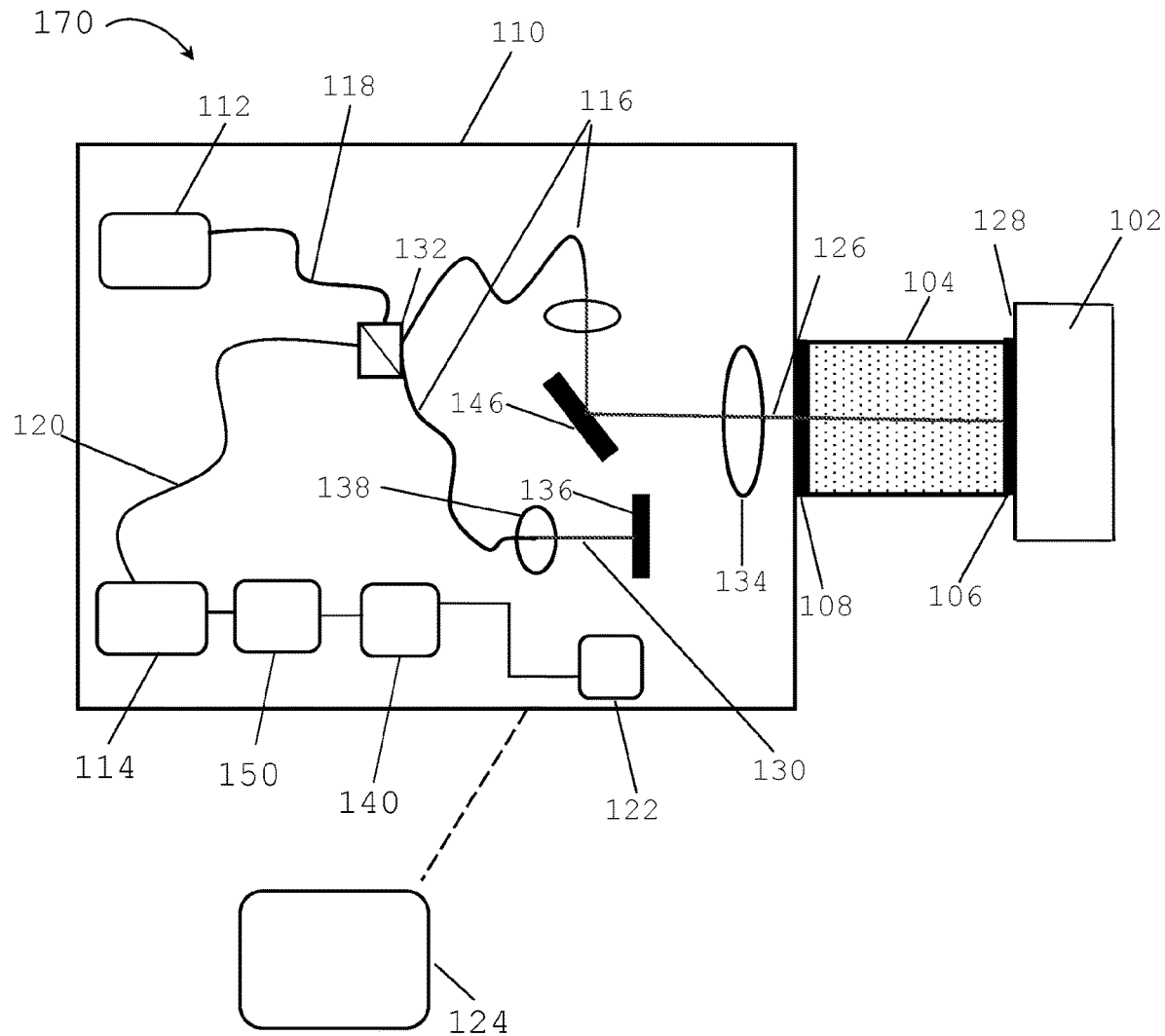
FIG. 4 is a schematic representation of a device for evaluating a mechanical property of a material in accordance with another embodiment of the present invention.

FIG. 3b illustrates the principle of determining a mechanical property, such as elasticity, of a material using the device and method in accordance with embodiments of the present invention. A relatively narrow band light source having a relatively long coherence length is used. Only one measurement is required if the initial thickness of the sensing layer is known. The interference signal detected from the interface 128 before application of a load and compression of the sensing layer 104 (see FIG. 3b, layer 104bc) appears to have an intensity corresponding to the maximum of the Gaussian function The interference signal detected from the interface 128 after application of a load and compression of the sensing layer 104 (see FIG. 3b, layer 104ac) has an intensity (i) along the Gaussian function that has decreased as compared to the intensity detected before compression. This is indicative that the difference between the optical sample pathlength 126 and the optical reference pathlength 130 has changed (and the interference conditions have changed indicating the change in layer thickness) in response to the applied load. FIG. 4 illustrates a device 170 used for obtaining an optical palpation image or map in accordance with an embodiment of the present invention. A scanning mirror 146 is used for scanning the sample signal across the sensing surface 106 of the sensing layer 104 such that an optical palpation image or map the sensing surface 106 can be obtained. The scanning mirror 146 may be an MEMS mirror (Micro Electro Mechanical System) or a galvanometer mirror.

It will also be understood that alternatively, it is envisaged that a vibrating or rotating optical fibre be used as the optical fibre 116 for directing the electromagnetic radiation towards the sensing surface 106 and for scanning the sample signal across the sensing surface 106 of the sensing layer 104 such that an optical palpation image or map of the sensing surface 106 can be obtained.

In another alternative embodiment, it is envisaged that a bundle of optical fibres 116 be used for directing the electromagnetic radiation towards the sensing surface 106 and for obtaining an optical palpation image or map of the sensing surface 106, wherein each pixel of the image obtained corresponds to information indicative of electromagnetic radiation reflected at the sensing surface 106 and received by a respective optical fibre 116 of the bundle.

Figure 5A:
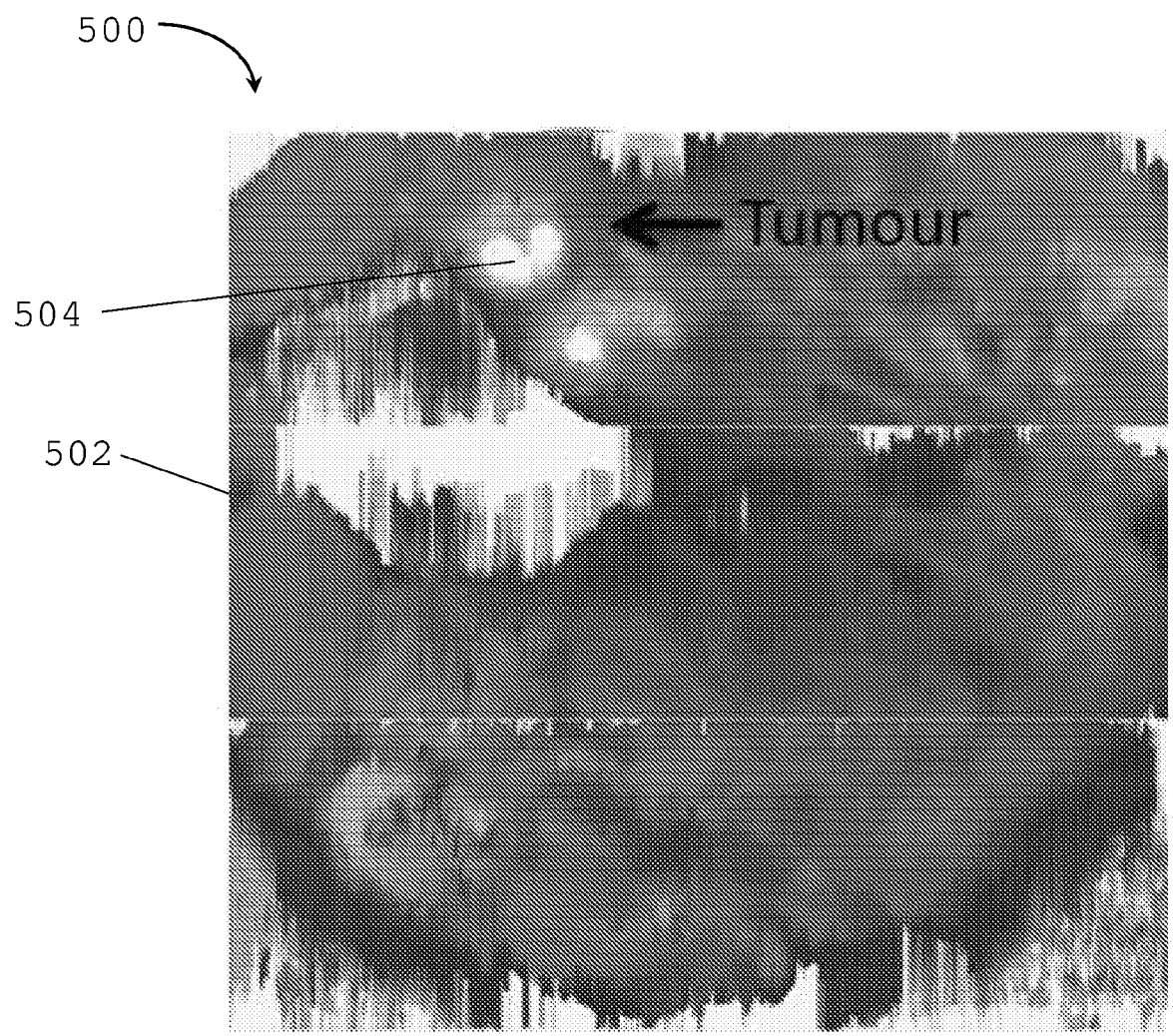
FIG. 5a is an image of a material obtained using a method and a device in accordance with an embodiment of the present invention.

FIG. 5a shows an optical palpation image 500 of tissue 502 obtained using a device such as device 170 described above. In this case the material is biological tissue that includes a tumour. A location of the tumour 504 (which is stiffer than healthy tissue) within healthy biological tissue is clearly identifiable.

Figure 5B:
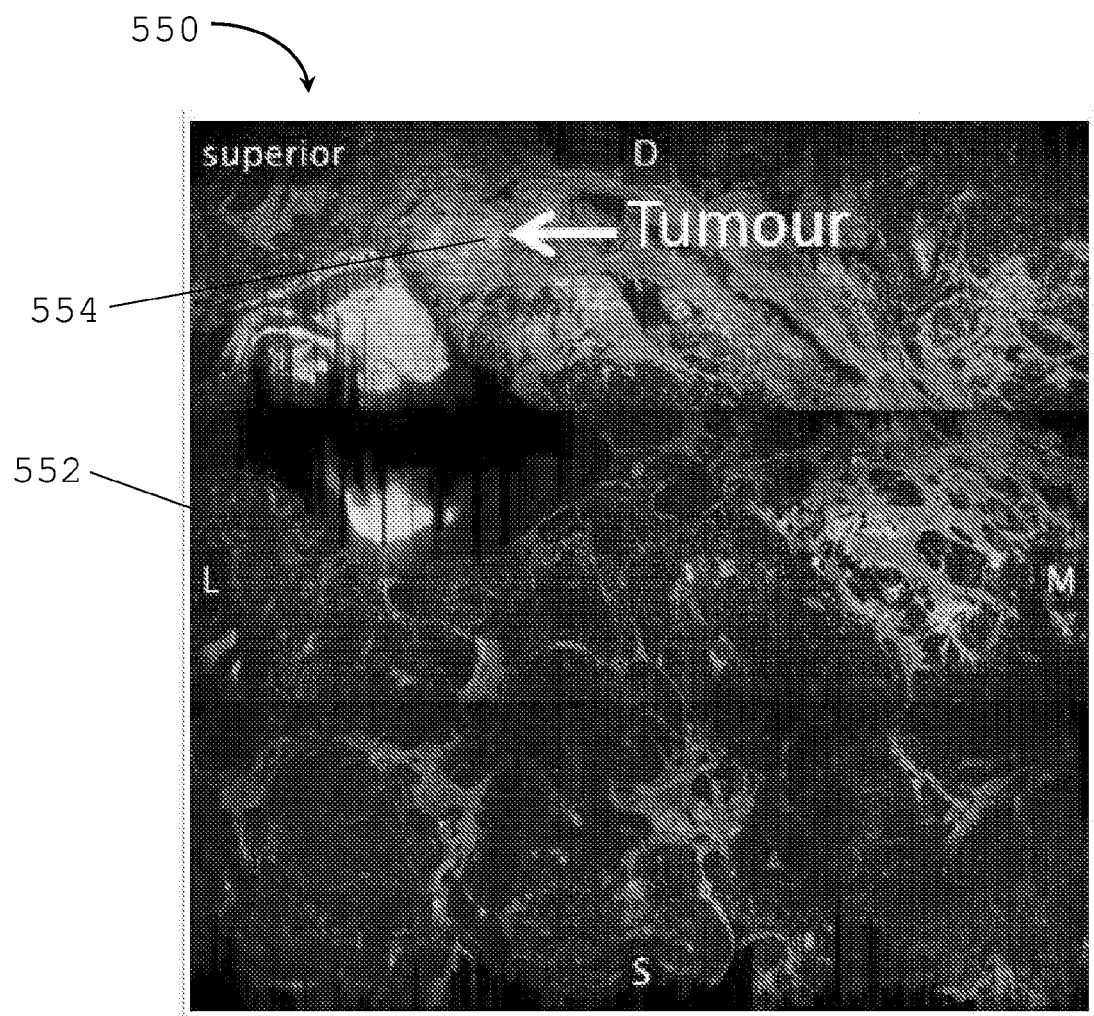
FIG. 5b is an image of a material obtained using OCT.

For comparison FIG. 5b shows an optical palpation image 550 obtained using an OCT imaging technique. FIG. 5b images the same biological tissue region 552 as FIG. 5a and also identifies the tumour 554.

Figure 6:
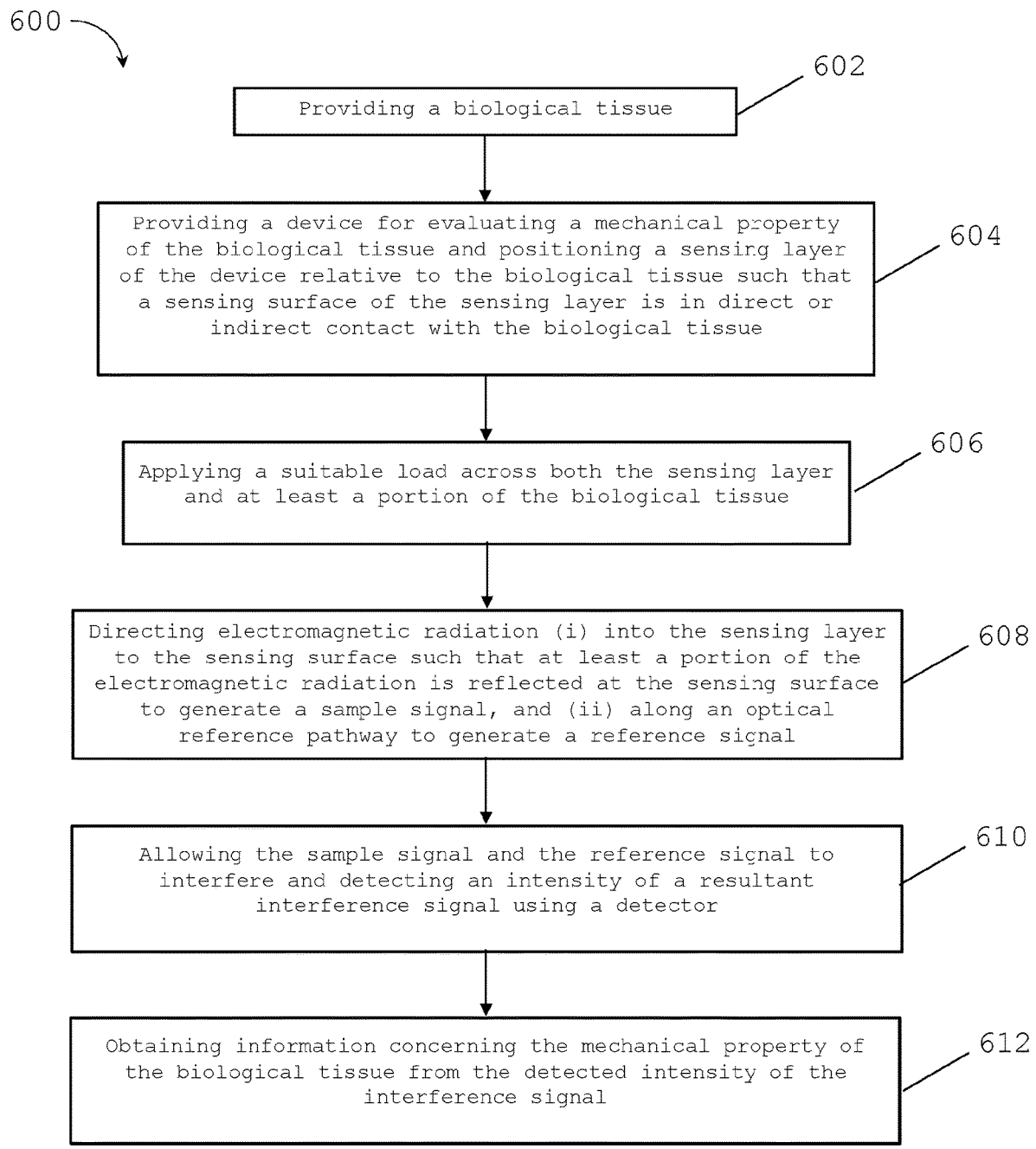
FIG. 6 is a flow chart of a method in accordance with an embodiment of the present invention.

FIG. 6 shows a flow chart of a method 600 for evaluating a mechanical property of a material or biological material in accordance with an embodiment of the present invention.

The method 600 comprises step 602, which provides the material 102. Step 604 provides a handheld device 100

The sensing layer 104 of the device 100 is positioned relative to the material 102 such that the sensing surface 106 is in contact with the material 102.

Step 606 applies a suitable load across both the sensing layer 104 and a portion of the underlying material 102.

Step 608 directs electromagnetic radiation along a sample path from the source 112 through the sensing layer 104 to the interface 128 between the sensing surface 106 and the material such that a portion of the electromagnetic radiation is reflected at the interface (see FIGS. 1 and 2). Step 608 also directs electromagnetic radiation emitted by the source 112 along a reference pathlength 130 to generate a reference signal (see FIGS. 1 and 2).

Step 610 allows the sample signal and the reference signal to interfere. A resultant interference signal is then detected using detector 114.

Step 612 obtains information concerning the mechanical property of the material 102, such as elasticity of the material 102, from the detected intensity of the interference signal. In one embodiment, the device 100 comprises an analog-to-digital converter 140 for converting an output of the detector 114 to digital data and a transmitter 142 for wireless transmission of the digital data from the device 100 to a computer 124, where the data can be processed. The data are processed to determine a change in thickness of the sensing layer 104 as a consequence of compression by application of the suitable load. Information concerning the mechanical property of the material 102 is then derived from the determination of the change in thickness of the sensing layer 104. For example, a stress experienced by the sensing layer 104 as a result of the application of the suitable load can be determined, which stress is indicative of the elasticity of the material 102.

The following will discuss further details of analysing the detected interference intensities.

The relationship between the intensity of the signal detected by the detector 114 and the thickness of the sensing layer 104 is defined as follows:

$$I_D = I_R + I_S + 2\sqrt{I_S I_R} \Re\{\gamma(\tau)\},$$

where $I_D$ is the intensity of the detected signal at detector 114, $I_R$ is the intensity of the reference signal, $I_S$ is the intensity of the sample signal, and $2\sqrt{I_S I_R}\Re\{\gamma(\tau)\}$ is the component of the interference signal between the sample signal and the reference signal. The $\Re$, component is the real part of complex coherence function $\gamma(\tau)$, where:

$$\gamma(\tau) = \exp\left\{-\left(\frac{\pi\Delta f\tau}{2\sqrt{\ln 2}}\right)^2\right\}\exp\{-i2\pi f\tau\},$$

wherein $$\exp\{-i2\pi f\tau\} = \cos(2\pi f\tau) + i\sin(2\pi f\tau)$$

and $\tau$ is the time delay between the detected reference and sample signals due to the difference in their relative path lengths, i.e., $\tau = \Delta L/c$, $\Delta L$ being the thickness of the sensing layer 104.

Thus $\Delta L$ can be measured and calculated from the detected $I_D$.

By measuring the intensity $I_D$ before and after the application of the suitable load, a change in the thickness $\Delta L$ of the sensing layer 104 can be measured. The change in the thickness $\Delta L$ of the sensing layer 104 can then be used to determine the stress experienced by the sensing layer 104. For determining the stress experienced at the sensing layer 104, strain $\varepsilon$ experienced by the sensing layer 104 as a result of the application of the suitable load is determined as follows:

$$\varepsilon = \frac{\Delta L(x, y) - \Delta L_0(x, y)}{\Delta L_0(x, y)}$$

wherein $\varepsilon$ relates to the strain of the sensing layer 104, $\Delta L_0$ relates to the initial thickness of the sensing layer 104 before application of the suitable load, $\Delta L$ relates to the change in thickness of the sensing layer 104 due to application of the suitable load, and (x,y) relates to a lateral position across an area of the sensing layer 104.

Then, stress experienced by the sensing layer 104 is determined based on the measured strain and a known stress-strain curve of the material of the sensing layer 104. The determined stress is indicative of the elasticity of the material.

The detector 114 is, in this example, a photodetector and detects the real component of the complex coherence function.

The intensity detected by the detector 114 is defined as follows:

$$I_D = I_R + I_S + 2\sqrt{I_S I_R}\exp\left\{-\left(\frac{\pi\Delta f\tau}{2\sqrt{\ln 2}}\right)^2\right\}\cos(2\pi f\tau)$$

The intensity value $I_S$ is influenced by the following factors:
1) the position of the interface 128 with respect to the focus of the lens 134 used to collimate the electromagnetic radiation propagating along the sample pathlength 126 (referred in the following as focus effect),
2) the angle of the interface 128 relative to the optical beam of electromagnetic radiation propagating along the sample pathlength 126 (referred in the following as tilt effect), and
3) the phase content of the signal.

The intensity of the reference signal is constant because the reference signal is provided by an optical reference pathlength that remains constant. In contrast to the sample signal and the interference signal, the intensity of the detected reference signal consequently will not depend on other factors.

In light of the relationship between $I_S$ and $I_D$, such factors also influence the $I_D$ value, which has consequences for the determination of $\Delta L$.

Figure 7A:
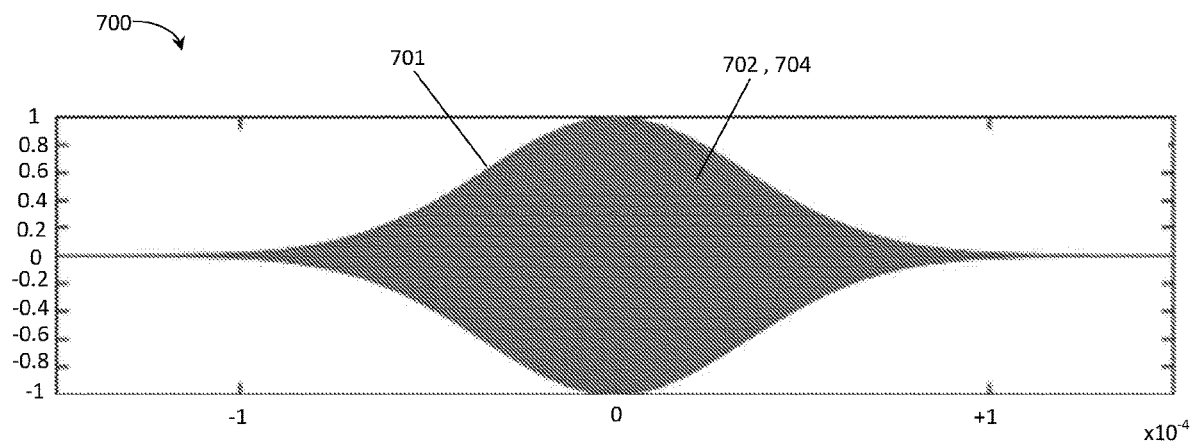
FIG. 7 (a) and (b) are a plot of magnitude and phase, respectively, of an intensity component detected using a method and a device in accordance with an embodiment of the present invention.
Figure 7B:
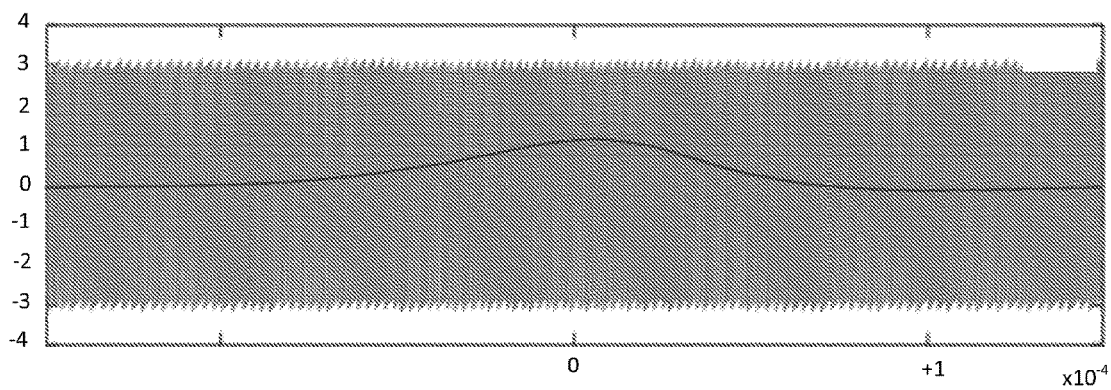

FIG. 7 (a) shows a plot 701 representing the real component 702 and imaginary component 704 of the complex coherence function $\gamma(\tau)$ (the components 702 and 704 are each oscillating components that are not resolved in FIG. 7(a) obtained using the handheld device and method in accordance with an embodiment of the present invention). The x axis of plot 700 corresponds to $\tau$ or $\Delta L$, and the y axis corresponds to the value of the intensity of the interference signal. FIG. 7(b) shows the corresponding phase. In this example a source 112 having a central wavelength of 1300 nanometres, and a low bandwidth of 15 nanometres, corresponding to a coherence length of around 50 micrometres, is used. The envelope 701 of the plotted components 702 and 704 is given by the term $$\exp\left\{-\left(\frac{\pi\Delta f\tau}{2\sqrt{\ln 2}}\right)^2\right\}$$

and is typically a Gaussian function.

FIG. 7 (a) illustrates that the width of the envelope is dependent on the bandwidth of the electromagnetic radiation emitted by the source 112.

Further, as illustrated in FIG. 7 (a), the envelope of the detected intensity of the interference signal changes from around 0 to a maximum of the envelope 701 as the difference between the length of the optical reference pathlength 130 and the length of the optical sample pathlength 126 varies.

As mentioned, τ is the time delay between the detected reference and sample signals due to the difference in their relative path lengths, i.e., τ=ΔL/c, ΔL being the thickness of the sensing layer 104. Accordingly, in order to determine ΔL, it is necessary to extract the term of amplitude of the interference component of measured intensity $I_D$, which corresponds to the term $$2\sqrt{I_S I_R} \exp\left\{-\left(\frac{\pi \Delta f \tau}{2\sqrt{\ln 2}}\right)^2\right\}.$$

The following will describe how the amplitude of the interference component or complex coherence function, and subsequently ΔL information, can be extracted.

Figure 8A:
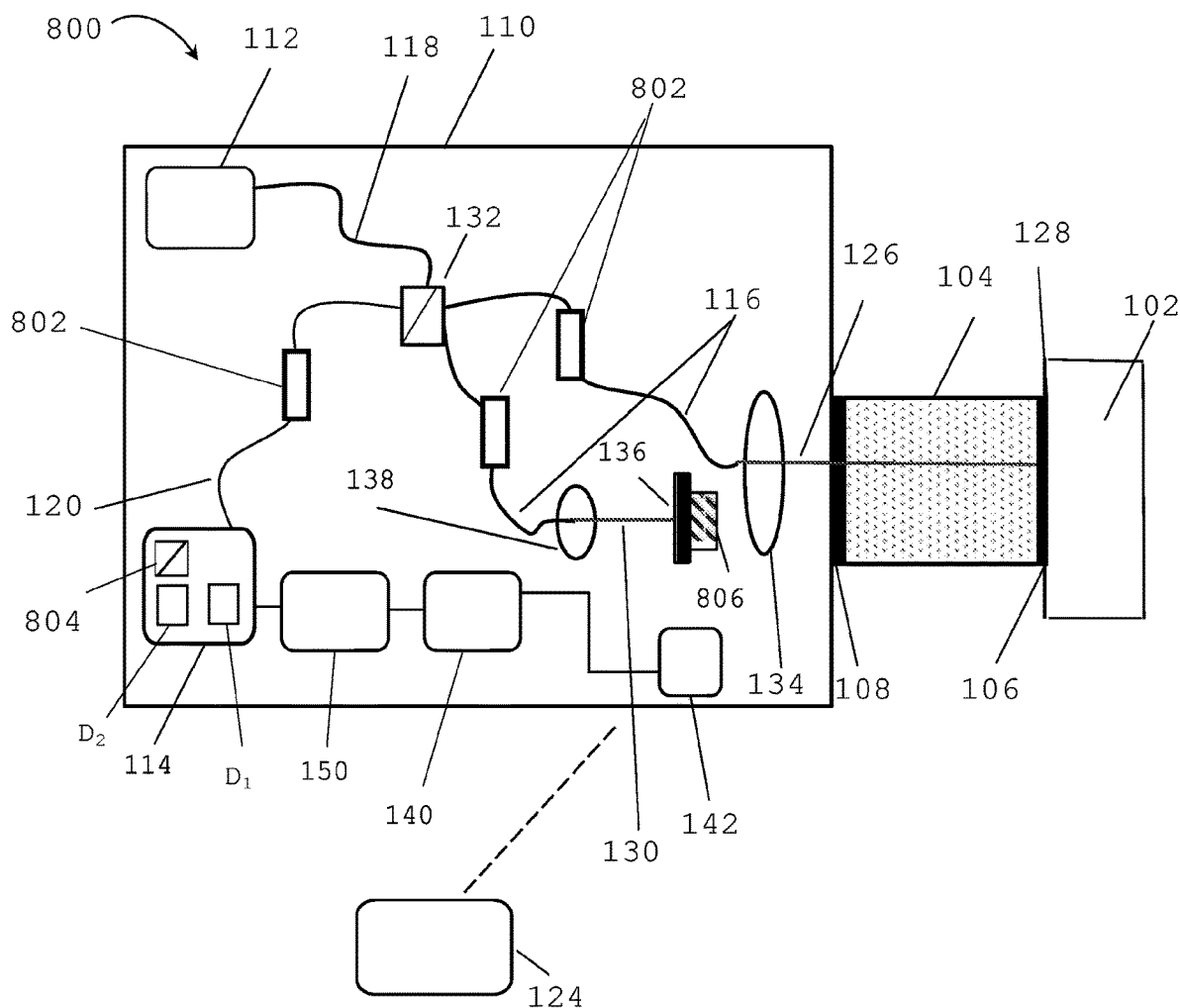
FIG. 8*a* is a schematic representation of a system used for evaluating a mechanical property of a material in accordance with a further embodiment of the present invention.

Referring to FIG. 8a, there is shown a schematic representation of a handheld device 800 used for determining ΔL in accordance with an embodiment of the present invention.

The device 800 comprises polarisation controllers 802 positioned along the optical sample pathway 126, the optical reference pathway 130 and the pathway 120 along which a sum of the reference signal and the optical signal travel past the optical beam splitter 132 towards the detector 114. The polarisation controllers 802 control the polarisation state of the respective signals. In particular, the optical reference signal is linearly polarised and the sample signal is circularly polarised.

Figure 8B:
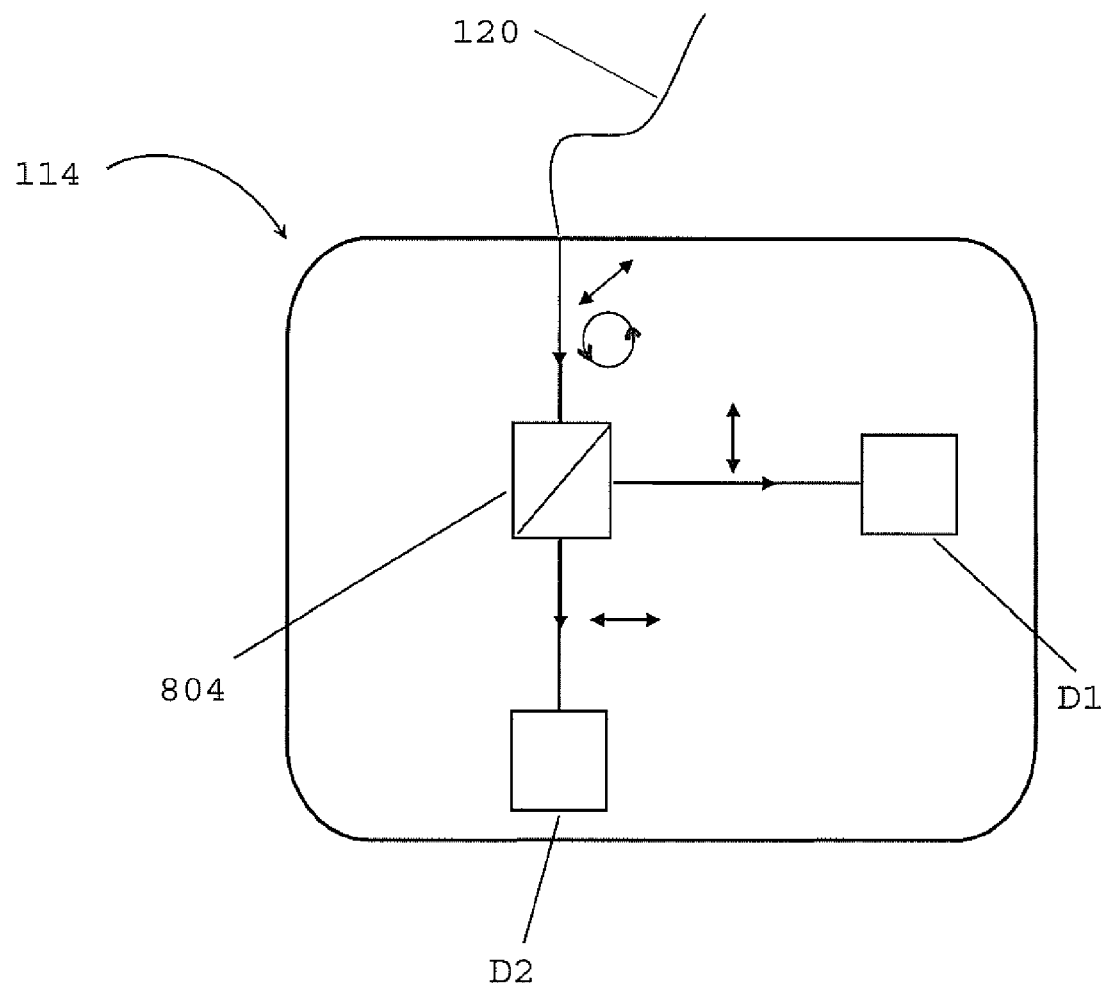
FIG. 8*b* is a schematic representation of a detector of a system used for evaluating a mechanical property of a material in accordance with the embodiment of the present invention illustrated in FIG. 8*a*.

Referring to FIG. 8b, the detector 114 receives an optical signal indicative of the reference signal linearly polarised and the sample signal circularly polarised.

Polarisation diversity detection is used and the detector 114 comprises a polarisation beam splitter 804 that splits the received optical signal associated with the reference signal and the sample signal into two signals having respective polarisation states that are orthogonal with respect to each other. The sample signal and the reference signal interfere, and two interference signals resulting from respective interferences of the sample signal and the reference signal at the respective polarisation states are obtained. The detector 114 further comprises two photodetectors $D_1$ and $D_2$ that detect respective intensities associated with the resultant interference signals having the respective polarisation states.

Specifically, the detector $D_1$ detects electromagnetic radiation that is formed by interference of signals from the optical sample pathlength 126 and the optical reference pathlength 130 with a 0-degree phase shift, and the detector $D_2$ detects electromagnetic radiation that is formed by interference of signals from the optical sample pathlength 126 and the optical reference pathlength 130 with a 90-degree phase shift. Two resulting signal intensities $I_{D1}$ and $I_{D2}$ are measured at $D_1$ and $D_2$ respectively:

$$I_{D1} = I_R + I_S + 2\sqrt{I_S I_R} \exp\left\{-\left(\frac{\pi \Delta f \tau}{2\sqrt{\ln 2}}\right)^2\right\} \cos(2\pi f \tau) \text{ and}$$

$$I_{D2} = I_R + I_S + 2\sqrt{I_S I_R} \exp\left\{-\left(\frac{\pi \Delta f \tau}{2\sqrt{\ln 2}}\right)^2\right\} \sin(2\pi f \tau)$$

The norm 2 of each of $I_{D2}$ and $I_{D2}$ are then combined so as to remove the influence of the cosine and sine terms and accordingly extract the term of amplitude of the interference signal $$2\sqrt{I_S I_R} \exp\left\{-\left(\frac{\pi \Delta f \tau}{2\sqrt{\ln 2}}\right)^2\right\}.$$

Figure 9A:
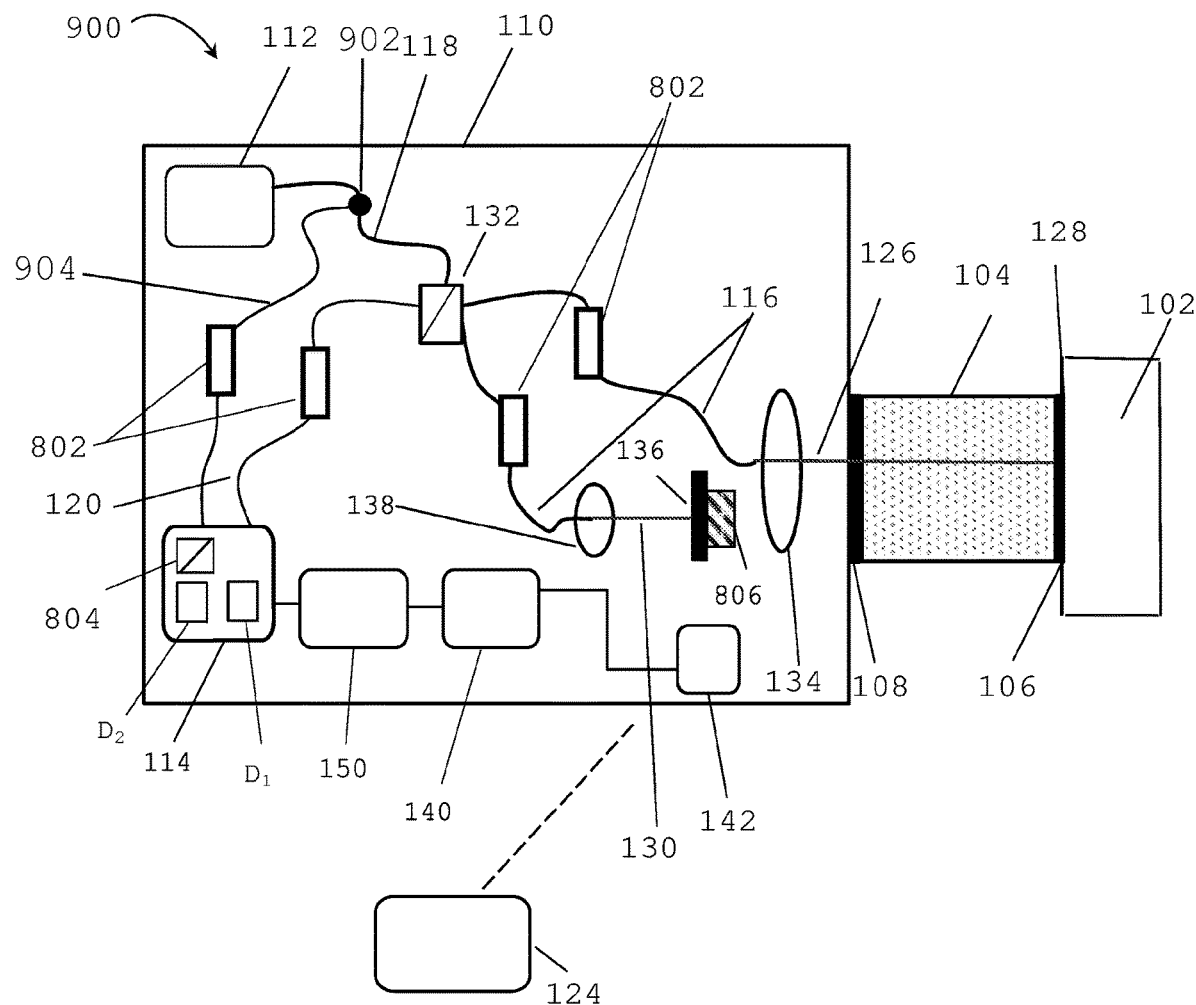
FIG. 9*a* is a schematic representation of a system used for evaluating a mechanical property of a material in accordance with an additional embodiment of the present invention.

FIG. 9a illustrates handheld device 900 used for determining ΔL in accordance with an alternative embodiment of the present invention for which a balanced detection method is used, which may allow improving the noise performance of the handheld device 800.

Figure 9B:
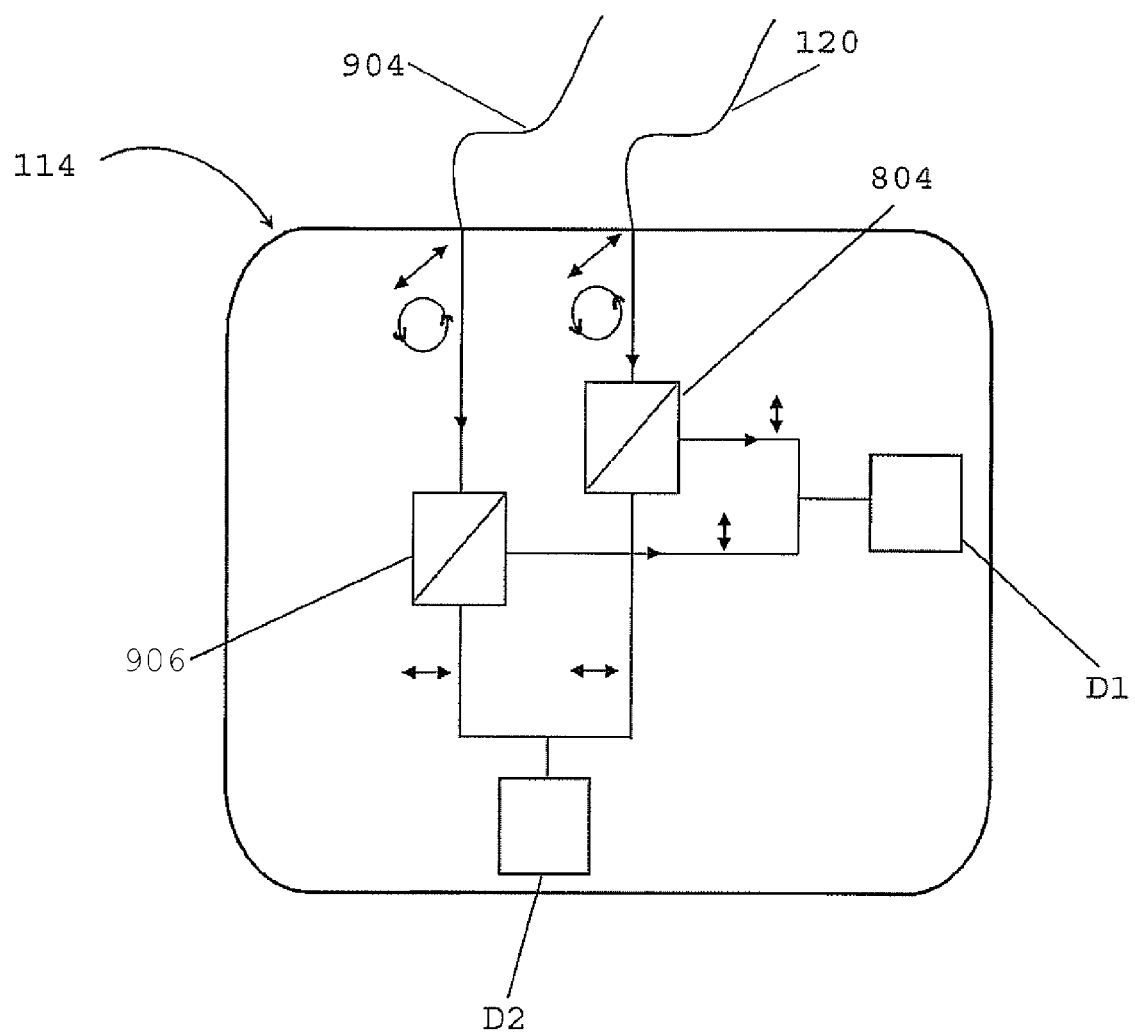
FIG. 9*b* is a schematic representation of a detector of a system used for evaluating a mechanical property of a material in accordance with the embodiment of the present invention illustrated in FIG. 9*a*.

In this particular embodiment, a circulator 902 is located along the pathway 118 between the source of electromagnetic radiation 112 and the optical beam splitter 132. As can also be seen more specifically in FIG. 9b, the detector 114 receives a signal associated with circularly polarised sample signal and linearly polarised reference signal traveling along the pathway 120, and additionally receives a signal associated with circularly polarised sample signal and linearly polarised reference signal that pass the optical beam splitter 132 and travel along the pathway 118, through the circulator 902, and are redirected to the detector 114 along pathway 904.

The detector 114 is a polarisation diversity detector and comprises two polarisation beam splitters 804 and 906. Each of the polarisation beam splitters 804 split the respective signals received by detector 114 into two signals having respective polarisation states that are orthogonal with respect to each other. Respective signals that are obtained from the respective polarisation beam splitters 804 and 906, and that have the same polarisation states, are allowed to interfere and intensities $I_{D1}$ and $I_{D2}$ associated with the resulting interference signals are detected by means of detectors $D_1$ and $D_2$.

If no tilt effect exists, a maximum amount of light will be collected at the detectors D1 and D2. However, if a tilt effect exists, a portion of the light will be lost when reflected at the interface 128. The focus effect will also affect the tilt effect.

Accordingly, even if the angle of the interface 128 relative to the optical beam of electromagnetic radiation propagating along the sample pathlength 126 is known, it would be advantageous to correct simultaneously for the effect of the focus and tilt mentioned above on $I_S$ and $I_D$, and as a result on the determination of ΔL based on the measured $I_{D1}$ and $I_{D2}$, without having to determine or measure independently the angle of the interface 128 relative to the optical beam of electromagnetic radiation propagating along the sample pathlength 126, and/or the position of the interface 128 with respect to the focus of the lens 134 used to collimate the electromagnetic radiation propagating along the sample pathlength 126.

In the present embodiment, a method of heterodyne detection is used to extract information regarding ΔL that is independent of both focus and tilt effects.

As can be seen in FIGS. 8a and 9a, an actuator 806 is positioned at the reference mirror 136 to induce vibrations on the reference mirror 136, resulting in a modulation of the reference signal, and consequently also, resulting in a modulation of the interference signal component $2\sqrt{I_S I_R} \Re\{\gamma(\tau)\}$. The resulting modulation corresponds to a modulation of the phase component of the reference signal and of the interference signal, as illustrated in FIG. 8. More specifically, the modulation of the reference signal by means of the actuator 806 results in a carrier modulation α(t) in the interference signal according to the following equations:

$$I_{D1} = I_R + I_S + 2\sqrt{I_S I_R} \exp\left\{-\left(\frac{\pi \Delta f \tau}{2\sqrt{\ln 2}}\right)^2\right\} \cos(2\pi f \tau + \alpha(t)) \text{ and}$$

$$I_{D2} = I_R + I_S + 2\sqrt{I_S I_R} \exp\left\{-\left(\frac{\pi \Delta f \tau}{2\sqrt{\ln 2}}\right)^2\right\} \sin(2\pi f \tau + \alpha(t))$$

In this embodiment, the actuator 806 is a piezoelectric actuator. The person skilled in the art will understand that other means to modulate the reference signal may be used, such as non-linear optical modulator.

Using high-pass and low-pass filters 150 positioned past the detectors $D_1$ and $D_2$, the following components can be extracted from the detected signal intensities $I_{D1}$ and $I_{D2}$:

$$I_{D1;DC} = I_R + I_S, \text{ and}$$

$$I_{D1,AC} = 2\sqrt{I_S I_R} \exp\left\{-\left(\frac{\pi \Delta f \tau}{2\sqrt{\ln 2}}\right)^2\right\} \cos(2\pi f \tau + \alpha(t))$$

$$I_{D2;DC} = I_R + I_S, \text{ and}$$

$$I_{D2,AC} = 2\sqrt{I_S I_R} \exp\left\{-\left(\frac{\pi \Delta f \tau}{2\sqrt{\ln 2}}\right)^2\right\} \sin(2\pi f \tau + \alpha(t))$$

Multiple measurements of $I_{D1;DC}$, $I_{D1;AC}$, $I_{D2;DC}$ and $I_{D2;AC}$ are collected over a detection time which is chosen to be greater than the carrier frequency of the signals. The data are then calibrated manually or automatically, which may comprise regression analysis or machine learning, into a measurement of $I_D$, which is purely dependent on $\tau$, and consequently $\Delta L$ (independent of tilt and focus effects).

The angle of the interface 128 relative to the optical beam of electromagnetic radiation propagating along the sample pathlength 126 can be for example measured based on the total ratio of intensities $ID_1$ and $ID_2$. In this example, a dielectric coating is positioned on the interface 128 of the sensing layer 104. The dielectric coating influences the reflection of the incident polarised optical beam of electromagnetic radiation, depending on its polarisation state and based on the angle of the interface 128 relative to the optical beam of electromagnetic radiation.

In another example, two or more vibrating (multiplexed) reference mirrors may be used along the optical reference pathlength, and measurements are obtained for the reference positions, which are within the coherence length of the electromagnetic radiation emitted by the source 112. A relative difference between the measurements will cancel out, and therefore the result will be independent of the tilt effect.

Figure 10:
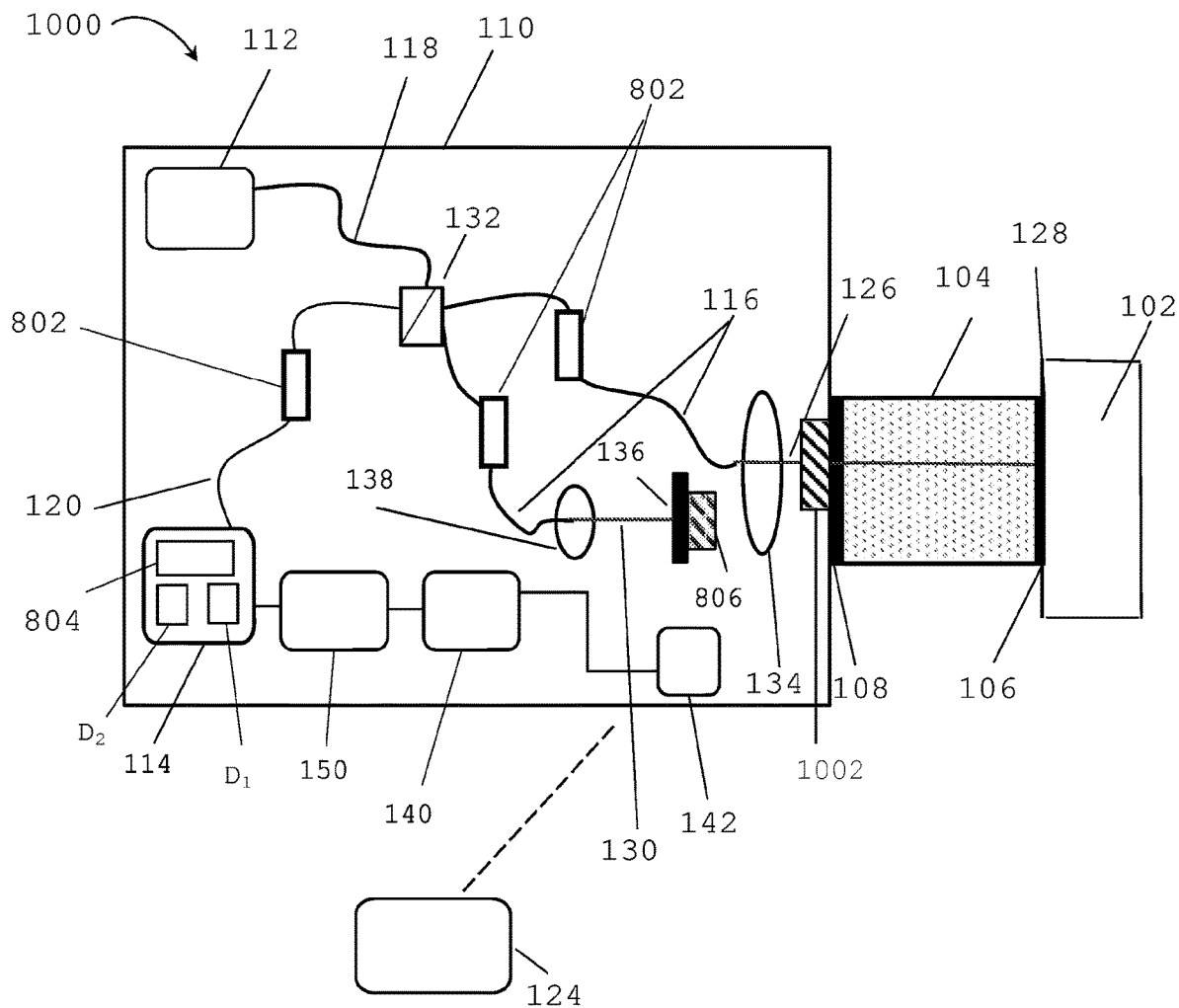
FIG. 10 is a schematic representation of a system used for evaluating a mechanical property of a material in accordance with an alternative embodiment of the present invention.

Referring now to FIG. 10, there is shown a schematic representation of a handheld device 1000 used for determining $\Delta L$ in accordance with another embodiment of the present invention.

The handheld device 1000 comprises all elements of the handheld device 800, however in this embodiment, an actuator 1002 is additionally positioned at the opposite surface 106 of the sensing layer 104 to modulate the phase content of the sample signal, and subsequently modulate the interference signal component. By modulating both the reference signal and the sample signal, very small variations in $\Delta L$ may be measured, as compared if the sample signal is not modulated, and variations in $\Delta L$ may be measured in a substantially more accurate and precise manner. More specifically, modulating both the reference signal and the sample signal may allow achieving a displacement sensitivity and detecting variations in $\Delta L$ in the sub-nanometre range.

The actuator 1002, when actuated, causes a compression of the sensing layer 104. Intensities $I_{D1}$ and $I_{D2}$, which are phase shifted by 90 degrees, are detected at time $t_1$ by respective detectors $D_1$ and $D_2$ when the actuator 1002 is not actuated, and intensities $I_{D1}$ and $I_{D2}$ are detected at time $t_2$ by respective detectors $D_1$ and $D_2$ when the actuator 1002 is actuated.

The on-off actuation of the actuator 1002 is performed at a rate that is substantially much slower than the speed at which the detectors $D_1$ and $D_2$ can detect electromagnetic radiation and measure intensities, so that corresponding intensities $I_{D1}$ and $I_{D2}$ can be measured.

The change in thickness of the sensing layer 104 that can be detected is typically less than half the wavelength of the electromagnetic radiation emitted by the source 112, and can be identified according to the following equation:

$$\delta L = \frac{\lambda_o \left[\tan^{-1}\left(\frac{I_{D2;AC;t2}}{I_{D1;AC;t2}}\right) - \tan^{-1}\left(\frac{I_{D2;AC;t1}}{I_{D1;AC;t1}}\right)\right]}{4\pi n}$$

Where λo is the central wavelength of the electromagnetic radiation emitted by the source 112, and n is the refractive index of the sensor. The values of $I_{D1;AC}$ and $I_{D2;AC}$ are obtained using the method presented above using polarisation diversity detection, heterodyne detection and filtering the signals with high pass and low pass filters.

Figure 11:
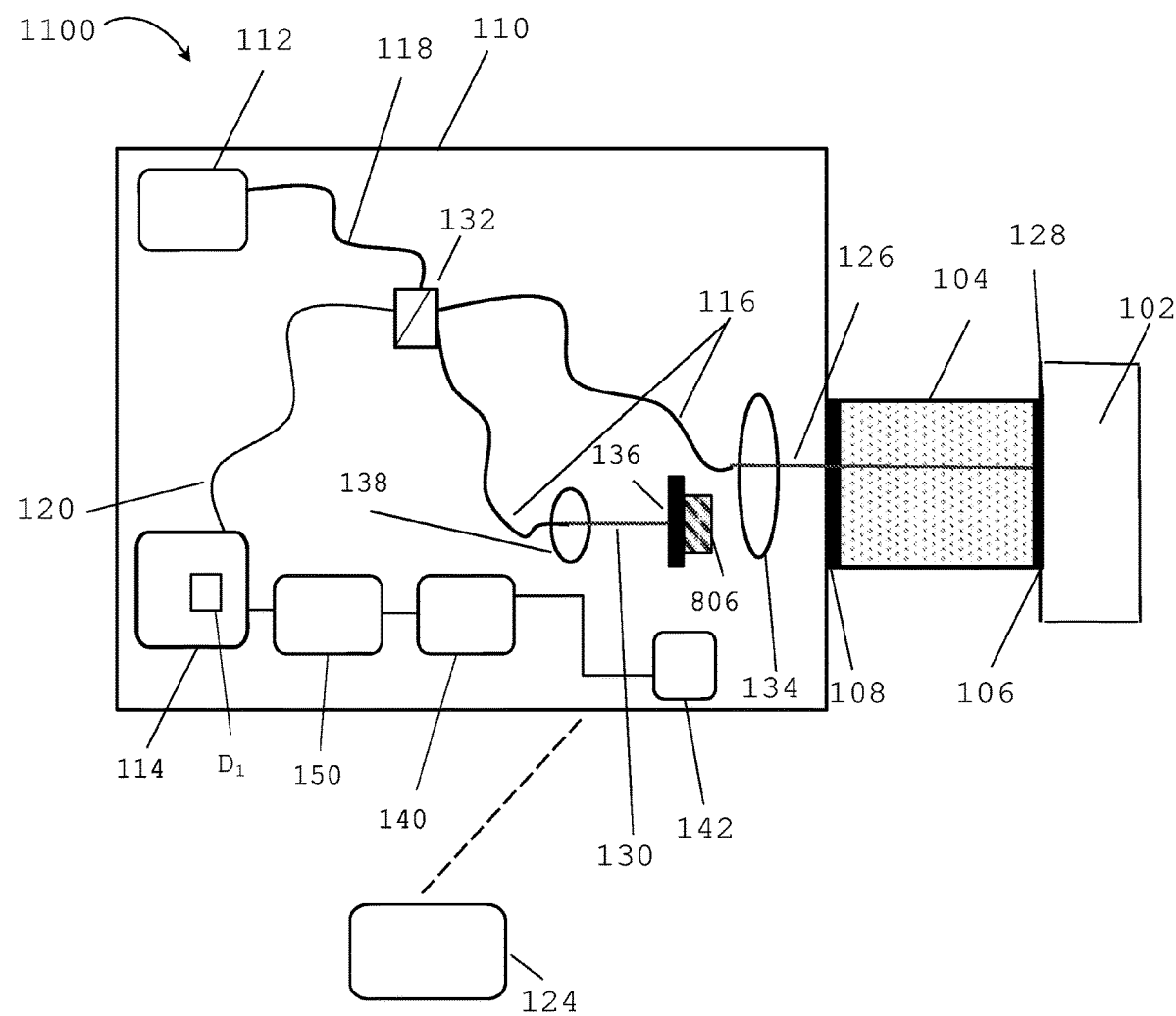
FIG. 11 is a schematic representation of a system used for evaluating a mechanical property of a material in accordance with another embodiment of the present invention.

FIG. 11 further illustrates a handheld device 1100 in accordance with another alternative embodiment wherein the handheld device 1100 does not comprise polarisation controllers. In this embodiment, the actuator 806 is positioned at the reference mirror 136 to induce vibrations on the reference mirror 136 at an amplitude that is a few times higher than the wavelength of the electromagnetic radiation emitted by the source 112. As a result, the phase content of interference signal component $2\sqrt{I_S I_R} \Re\{\gamma(\tau)\}$ is modulated by multiples of $2\pi$.

The detector 114 comprises a single photodetector $D_1$ that detects intensities associated with respective resulting interference signals over a detection time period. An average of the intensities detected over the detection time period is then determined, from which the value of $\tau$ and consequently $\Delta L$ can be extracted.

The mechanical property of the material 102, such as the elasticity, can further be quantitatively determined by calculating the Young's modulus, a relation between the determined stress experienced by the sensing layer 104 and a determined strain experienced by the material 102. In this embodiment, the Young's modulus E of the material 102 is determined as follows:

$$E = \frac{\sigma_{sensing\,layer\,104}}{\varepsilon_{biological\,tissue\,102}}$$

Wherein E relates to the Young's modulus of the material 102, $\sigma_{sensing\,layer\,104}$ relates to the determined stress experienced by the sensing layer 104, and $\varepsilon_{material\,102}$ relates to strain distributed within the material 102 in response to the application of the suitable load.

The strain distributed within the material 102 as a result of the application of the suitable load may be determined by measuring a relative displacement of the material 102 as a result of the application of the suitable load. This can be performed by repositioning the lens 134 so as to focus the electromagnetic radiation directed along the optical sample pathlength 126 into the material 102.

Modifications and variations as would be apparent to a skilled addressee are determined to be within the scope of the present invention.

The invention claimed is:

1. A method of evaluating a mechanical property of a material, the method comprising:
   providing the material;
   providing a device for evaluating the mechanical property of the material, the device comprising:
      a sensing layer having a thickness, a sensing surface and an opposite surface, the sensing layer being deformable such that, when the sensing surface is in direct or indirect contact with the material and a suitable load is applied across both the sensing layer and at least a portion of the material, the sensing layer deforms and the sensing surface moves relative to the opposite surface;
      a source of electromagnetic radiation in optical communication with the sensing layer, the source being arranged for generating electromagnetic radiation having a coherence length that is of the same order of magnitude as the thickness of the sensing layer or longer than the thickness of the sensing layer; and
      a detector for detecting the electromagnetic radiation and being in optical communication with the sensing layer and arranged for receiving the electromagnetic radiation after the electromagnetic radiation is reflected at the interface at the sensing surface of the sensing layer;
   the method further comprising:
   positioning the sensing layer relative to the material such that the sensing surface is in direct or indirect contact with the material;
   applying the suitable load across both the sensing layer and at least a portion of the material whereby the sensing layer deforms and the interface at the sensing surface moves relative to a condition in which no load is applied;
   directing the electromagnetic radiation to the interface at the sensing surface such that at least a portion of the electromagnetic radiation is reflected at the interface at whereby a first signal is generated;
   directing electromagnetic radiation along a second optical pathlength to generate a second signal;
   allowing the first signal and the second signal to interfere and detecting an intensity associated with a resultant interference signal using the detector; and
   determining information concerning the mechanical property of the material from the detected intensity of the interference signal.

2. The method of claim 1, wherein determining information concerning the mechanical property comprises determining a relative position of the interface at the sensing surface, with the length of the second optical path being fixed prior to application of the load and with no variation in the length of the second optical path being required to measure a distance that an external layer boundary or internal boundary has moved due to the application of the suitable load.

3. The method of claim 1, wherein the step of directing the electromagnetic radiation to the interface at the sensing surface comprises directing the electromagnetic radiation into and through the sensing layer to the sensing surface.

4. The method of claim 1, comprising determining a change in thickness of the sensing layer, the sensing layer having a predetermined known relaxed thickness being the thickness that the layer has when no load is applied, the change in thickness of the sensing layer being determined using the known relaxed thickness and a change in relative position of the interface at the sensing surface as a consequence of the deformation when the load is applied.

5. The method of claim 4, wherein the step of determining information concerning the mechanical property of the material comprises determining the change in thickness of the sensing layer from the detected intensity of the interference signal and determining the mechanical property of the material from the determined change in thickness of the sensing layer.

6. The method of claim 1, comprising determining the change in thickness of the sensing layer from a single interference signal.

7. The method of claim 1, comprising determining the change in thickness of the sensing layer from two interference signals.

8. The method of claim 7, wherein the two interference signals are generated by reflections at top and bottom interfaces of the sensing layer.

9. The method of claim 1, wherein determining information concerning the mechanical property of the material comprises determining a change in an optical pathlength difference between the first signal and the second signal from a measured intensity of the detected interference signal in response to the suitable load applied to the sensing layer and the material.

10. The method of claim 9, wherein determining the information concerning the mechanical property comprises determining the information from the determined change in optical pathlength difference.

11. The method of claim 1, wherein the mechanical property is elasticity or viscoelasticity and determining information concerning the mechanical property comprises determining a stress experienced by the sensing layer based on the determined change in optical pathlength difference.

12. The method of claim 1, wherein the source of electromagnetic radiation is arranged for generating electromagnetic radiation having a coherence length that provides an interference signal for a range of different thicknesses of the sensing layer without adjusting the length of the second optical path.

13. A handheld device for evaluating a mechanical property of a material, the device comprising:
   a sensing layer having a thickness, an exposed sensing surface and an opposite surface, the sensing layer being deformable such that, when the sensing surface is in direct or indirect contact with the material and a suitable load is applied across both the sensing layer and at least a portion of the material, the sensing layer deforms and the sensing surface moves relative to the opposite surface;
   a source of electromagnetic radiation in optical communication with the sensing layer, the source being arranged for generating electromagnetic radiation having a coherence length that is of the same order of magnitude as the thickness of the sensing layer or longer than the thickness of the sensing; and a detector for detecting the electromagnetic radiation and being in optical communication with the sensing layer and arranged for detecting electromagnetic radiation reflected at the interface at the sensing surface of the sensing layer;

wherein the device comprises:

a first optical pathlength in use providing a first signal, the first signal being a signal that is reflected at the sensing surface of the sensing layer; and a second optical pathlength in use providing a second signal; and wherein the detector is positioned to detect both the first signal and the second signal whereby the detector detects in use an intensity associated with an interference signal and information concerning the mechanical property can be determined from the intensity of the interference signal.

14. The device of claim 13, wherein the sensing layer has a thickness ranging from a few micrometres to a few centimetres when it is uncompressed, the sensing surface and the opposite surface (or the stationary surface) being separated from each other by a distance of a few micrometres to a few centimetres when the sensing layer is uncompressed.

15. The device of claim 13, wherein the sensing layer comprises, or is formed from, a translucent or transparent deformable material such as a gel, or an elastomer.

16. The device of claim 13, wherein the light source has a coherence length ranging from the thickness of the sensing layer to a length that corresponds to a multiple of the thickness of the sensing layer.

17. The device of claim 13, wherein the device comprises an oscillation or vibration element positioned at the mirror and/or the sensing layer for generation of an oscillating signal of the electromagnetic radiation.

18. The device of claim 17, wherein the device comprises polarisation controllers and polarisation filters to modify and control a polarisation state of the first signal and the second signal.

19. The device of claim 17, wherein the detector further comprises a polarising beam splitter arranged to split an optical signal indicative of the detected first signal and second signal into at least two signals having respective polarisations.

20. The device of claim 19, wherein the detector comprises respective detector portions for independent detection of the at least two signals having the respective polarisations.

* * * * *